(12) United States Patent
Schneider et al.

(10) Patent No.: US 10,390,998 B2
(45) Date of Patent: Aug. 27, 2019

(54) PROCESS AND APPARATUS FOR MANUFACTURING AN ABSORBENT ARTICLE USING A LASER SOURCE

(71) Applicant: The Procter & Gamble Company, Cincinnati, OH (US)

(72) Inventors: Uwe Schneider, Cincinnati, OH (US); Pablo Ibarrarazo, Liberty Township, OH (US); Klaus Eimann, Zellingen (DE); Michael Joseph Page, Cincinnati, OH (US); Bradley Edward Walsh, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 300 days.

(21) Appl. No.: 14/934,197

(22) Filed: Nov. 6, 2015

(65) Prior Publication Data
US 2016/0128874 A1 May 12, 2016

Related U.S. Application Data

(60) Provisional application No. 62/076,513, filed on Nov. 7, 2014.

(51) Int. Cl.
*A61F 13/15* (2006.01)
*B23K 26/359* (2014.01)

(52) U.S. Cl.
CPC .. *A61F 13/15723* (2013.01); *A61F 13/15593* (2013.01); *A61F 13/15739* (2013.01);
(Continued)

(58) Field of Classification Search
CPC .......... A61F 13/15723; A61F 13/15593; A61F 13/15739; A61F 13/15756; A61F 13/15764; B23K 26/359
See application file for complete search history.

(56) References Cited

U.S. PATENT DOCUMENTS

| 3,560,291 A | 2/1971 | Foglia et al. |
| 3,848,594 A | 11/1974 | Buell |

(Continued)

FOREIGN PATENT DOCUMENTS

| EP | 0 731 029 B1 | 6/1998 |
| EP | 0 868 251 B1 | 11/2004 |

(Continued)

OTHER PUBLICATIONS

PCT International Search Report dated Jan. 28, 2016, 13 pages.

*Primary Examiner* — Seyed Masoud Malekzadeh
*Assistant Examiner* — Taryn Trace Willett
(74) *Attorney, Agent, or Firm* — Andrew J. Hagerty; Sarah M. DeCristofaro

(57) ABSTRACT

The present disclosure relates to methods and apparatuses for assembling absorbent articles, and more particularly, methods and apparatuses for imparting a line of weakness into one or more layers of an advancing substrate. The advancing substrate may be a belt assembly including an outer layer, an inner layer, and one or more elastic strands disposed between the outer layer and the inner layer. The belt assembly may be rotated on a process member about a longitudinal axis of rotation. The process member may advance the belt assembly to a first laser source. The first laser source imparts a line of weakness into the belt assembly. A trim removal member may be used to separate the line of weakness forming a trim portion and a separation edge.

22 Claims, 23 Drawing Sheets

(52) U.S. Cl.
CPC .. *A61F 13/15756* (2013.01); *A61F 13/15764* (2013.01); *B23K 26/359* (2015.10)

(56) References Cited

U.S. PATENT DOCUMENTS

| | | | |
|---|---|---|---|
| 3,860,003 A | 1/1975 | Buell | |
| 4,116,892 A | 9/1978 | Schwarz | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,846,815 A | 7/1989 | Scripps | |
| 4,888,231 A | 12/1989 | Angstadt | |
| 4,894,060 A | 1/1990 | Nestegard | |
| 4,909,803 A | 3/1990 | Aziz et al. | |
| 4,946,527 A | 8/1990 | Battrell | |
| 5,151,092 A | 9/1992 | Buell et al. | |
| 5,167,897 A | 12/1992 | Weber et al. | |
| 5,221,274 A | 6/1993 | Buell et al. | |
| 5,360,420 A | 11/1994 | Cook et al. | |
| 5,393,360 A | 2/1995 | Bridges et al. | |
| 5,562,646 A | 10/1996 | Goldman et al. | |
| 5,599,335 A | 2/1997 | Goldman et al. | |
| 5,622,581 A * | 4/1997 | Ducker | A61F 13/15593 156/163 |
| 5,628,097 A | 5/1997 | Benson et al. | |
| 5,643,588 A | 7/1997 | Roe et al. | |
| 5,669,894 A | 9/1997 | Goldman et al. | |
| 5,674,216 A | 10/1997 | Buell et al. | |
| 5,702,551 A | 12/1997 | Huber et al. | |
| 5,760,369 A | 6/1998 | Wenkman | |
| 5,767,481 A | 6/1998 | Graf | |
| 5,817,271 A | 10/1998 | Congleton et al. | |
| 5,916,661 A | 6/1999 | Benson et al. | |
| 5,944,278 A | 8/1999 | Stevens, III et al. | |
| 5,968,025 A | 10/1999 | Roe et al. | |
| 6,056,682 A | 5/2000 | Belanger et al. | |
| 6,098,557 A | 8/2000 | Couillard et al. | |
| 6,107,537 A | 8/2000 | Elder et al. | |
| 6,107,539 A | 8/2000 | Palumbo et al. | |
| 6,118,041 A | 9/2000 | Roe et al. | |
| 6,153,209 A | 11/2000 | Vega et al. | |
| 6,191,382 B1 | 2/2001 | Damikolas | |
| 6,388,231 B1 | 5/2002 | Andrews | |
| 6,410,129 B2 | 6/2002 | Zhang et al. | |
| 6,414,264 B1 | 7/2002 | von Falkenhausen | |
| 6,426,444 B2 | 7/2002 | Roe et al. | |
| 6,500,377 B1 | 12/2002 | Schneider et al. | |
| 6,517,659 B1 | 2/2003 | VanderWerf et al. | |
| 6,524,443 B2 | 2/2003 | Doelle et al. | |
| 6,545,197 B1 | 4/2003 | Muller et al. | |
| 6,586,652 B1 | 7/2003 | Roe et al. | |
| 6,617,016 B2 | 9/2003 | Lana et al. | |
| 6,677,787 B1 | 1/2004 | Kumar et al. | |
| 6,743,321 B2 * | 6/2004 | Guralski | A61F 13/15593 156/204 |
| 6,790,798 B1 | 9/2004 | Suzuki et al. | |
| 6,794,604 B2 | 9/2004 | Herke et al. | |
| 6,825,393 B2 | 11/2004 | Roe et al. | |
| 6,838,040 B2 * | 1/2005 | Mlinar | B26F 3/002 225/2 |
| 6,861,571 B1 | 3/2005 | Roe et al. | |
| 6,862,615 B1 | 3/2005 | Wojcik et al. | |
| 7,032,278 B2 | 4/2006 | Kurtz, Jr. | |
| 7,144,479 B2 | 12/2006 | Davis et al. | |
| 7,306,388 B2 | 12/2007 | Acher | |
| 7,310,858 B2 | 12/2007 | Fleissner | |
| 7,528,343 B2 | 5/2009 | Lupinetti et al. | |
| 7,569,039 B2 | 8/2009 | Matsuda et al. | |
| 7,615,128 B2 | 11/2009 | Mikkelsen | |
| 8,138,449 B2 | 3/2012 | Matsuo et al. | |
| 8,440,043 B1 | 5/2013 | Schneider et al. | |
| 8,445,812 B2 | 5/2013 | Lupinetti et al. | |
| 8,540,612 B2 | 9/2013 | Skopek et al. | |
| 8,668,076 B2 | 3/2014 | Pasqualoni et al. | |
| 8,757,307 B2 | 6/2014 | Winter et al. | |
| 8,820,513 B2 | 9/2014 | Papsdorf et al. | |
| 8,822,009 B2 | 9/2014 | Riviere et al. | |
| 9,050,686 B2 | 6/2015 | Costin, Sr. et al. | |
| 9,149,394 B2 | 10/2015 | Rosani et al. | |
| 9,913,764 B2 * | 3/2018 | Thomas | A61F 13/4902 |
| 2001/0014798 A1 * | 8/2001 | Fernfors | A61F 13/15723 604/390 |
| 2002/0103468 A1 * | 8/2002 | Nakakado | A61F 13/15601 604/358 |
| 2003/0047695 A1 | 3/2003 | Zik et al. | |
| 2003/0135192 A1 * | 7/2003 | Guralski | A61F 13/15593 604/391 |
| 2004/0026384 A1 | 2/2004 | Mueller et al. | |
| 2004/0035521 A1 * | 2/2004 | Nakakado | A61F 13/15593 156/229 |
| 2004/0060648 A1 * | 4/2004 | Thorson | A61F 13/15699 156/258 |
| 2004/0097895 A1 | 5/2004 | Busam et al. | |
| 2004/0158212 A1 | 8/2004 | Ponomarenko et al. | |
| 2004/0159998 A1 | 8/2004 | Khalid | |
| 2005/0092146 A1 | 5/2005 | Carbone, II et al. | |
| 2005/0098008 A1 | 5/2005 | Henriksen | |
| 2005/0107764 A1 | 5/2005 | Matsuda et al. | |
| 2005/0145322 A1 * | 7/2005 | Hoffman | A61F 13/15593 156/160 |
| 2005/0214511 A1 | 9/2005 | Vogt et al. | |
| 2006/0090868 A1 | 5/2006 | Brownfield et al. | |
| 2007/0044608 A1 * | 3/2007 | Franke | A61F 13/15682 83/39 |
| 2008/0295984 A1 | 12/2008 | Miikki et al. | |
| 2008/0305298 A1 | 12/2008 | Lakshmi et al. | |
| 2009/0200280 A1 | 8/2009 | Piantoni et al. | |
| 2009/0312730 A1 | 12/2009 | LaVon et al. | |
| 2009/0324905 A1 * | 12/2009 | Welch | A61F 13/15593 428/198 |
| 2011/0048996 A1 | 3/2011 | Klaus et al. | |
| 2011/0125125 A1 * | 5/2011 | Schneider | A61F 13/551 604/385.23 |
| 2012/0061015 A1 | 3/2012 | LaVon et al. | |
| 2012/0061016 A1 | 3/2012 | LaVon et al. | |
| 2012/0079926 A1 | 4/2012 | Long et al. | |
| 2012/0312869 A1 | 12/2012 | Fike et al. | |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 * | 10/2013 | Schneider | A61F 13/15593 156/161 |
| 2013/0255865 A1 | 10/2013 | Brown et al. | |
| 2013/0277341 A1 | 10/2013 | Dvorkin | |
| 2013/0334739 A1 | 12/2013 | Miller et al. | |
| 2014/0110037 A1 * | 4/2014 | Verboomen | A61F 13/15747 156/66 |
| 2014/0171895 A1 * | 6/2014 | Thomas | A61F 13/49012 604/385.3 |
| 2015/0040367 A1 | 2/2015 | Wright et al. | |
| 2015/0079359 A1 | 3/2015 | Costin, Jr. | |
| 2015/0123318 A1 | 5/2015 | Sestini et al. | |
| 2015/0225890 A1 | 8/2015 | Canonico et al. | |
| 2016/0128877 A1 * | 5/2016 | Chandrasekaran | C09J 7/0296 24/306 |
| 2016/0354254 A1 * | 12/2016 | Eimann | A61F 13/15764 |
| 2017/0189999 A1 * | 7/2017 | Bookbinder | B23K 26/402 |
| 2017/0239100 A1 * | 8/2017 | Schmitz | A61F 13/15756 |
| 2018/0057304 A1 * | 3/2018 | Fritz | B65H 57/14 |

FOREIGN PATENT DOCUMENTS

| | | |
|---|---|---|
| EP | 1 820 634 A1 | 8/2007 |
| JP | 2004223238 | 8/2004 |
| JP | 2011/125641 A | 6/2011 |
| JP | 2011126660 | 6/2011 |
| WO | WO 2006/083127 A1 | 8/2006 |
| WO | WO 2007/122284 A1 | 11/2007 |
| WO | WO 2011/083205 A1 | 7/2011 |

(56) References Cited

FOREIGN PATENT DOCUMENTS

| WO | WO 2012/049267 A1 | 4/2012 |
| WO | WO 2014/001217 A1 | 1/2014 |
| WO | WO 2014/131813 A1 | 9/2014 |
| WO | WO 2014/183210 A1 | 11/2014 |
| WO | WO 2014/208636 A1 | 12/2014 |
| WO | WO 2014/208637 A1 | 12/2014 |
| WO | WO 2014/208638 A1 | 12/2014 |
| WO | WO 2014/208639 A1 | 12/2014 |
| WO | WO 2014/208640 A1 | 12/2014 |
| WO | WO 2014/208641 A1 | 12/2014 |
| WO | WO 2014/208642 A1 | 12/2014 |
| WO | WO 2015/022612 A1 | 2/2015 |
| WO | WO 2015/159204 A1 | 10/2015 |
| WO | WO 2015/159207 A1 | 10/2015 |
| WO | WO 2017/105889 A1 | 6/2017 |

\* cited by examiner

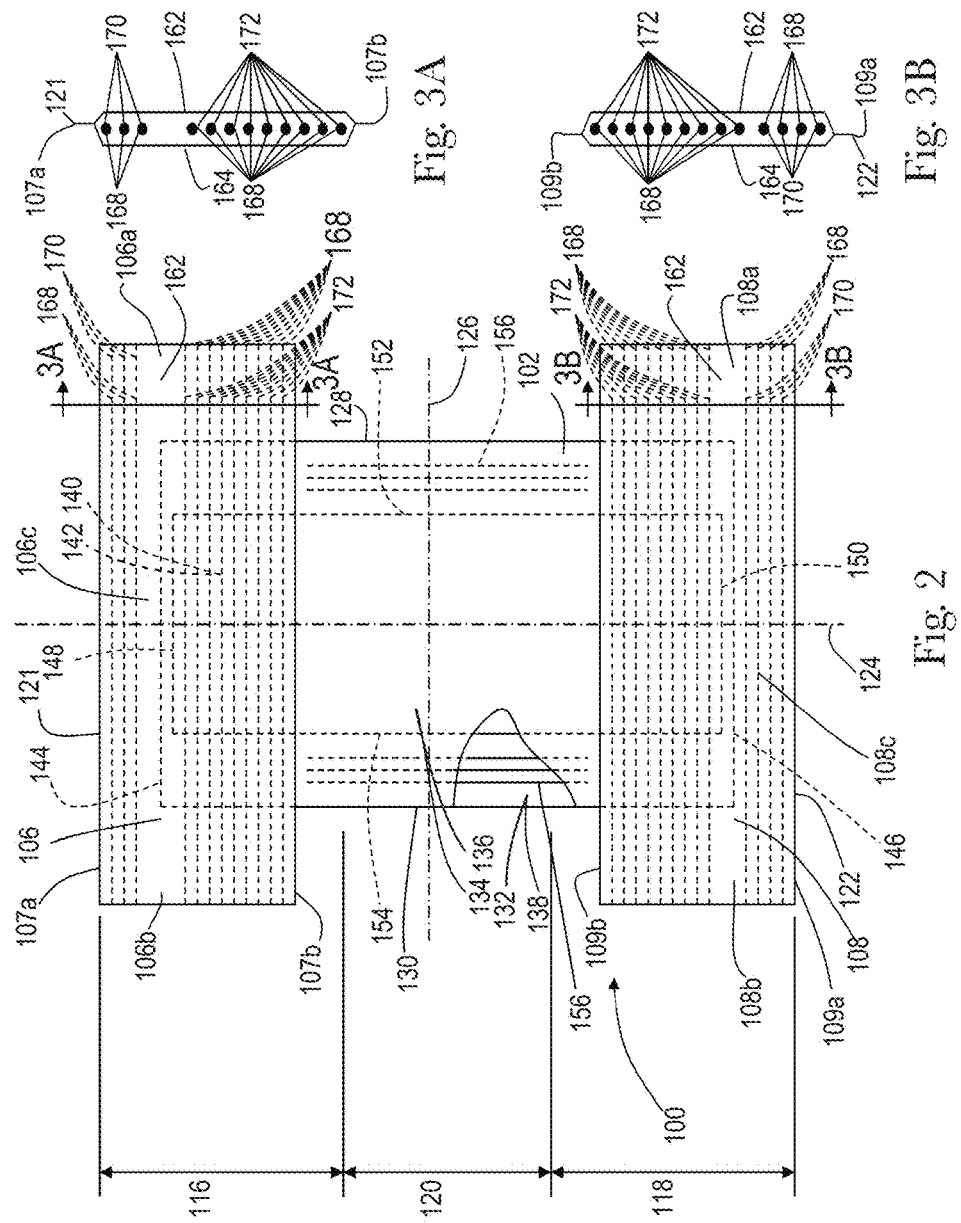

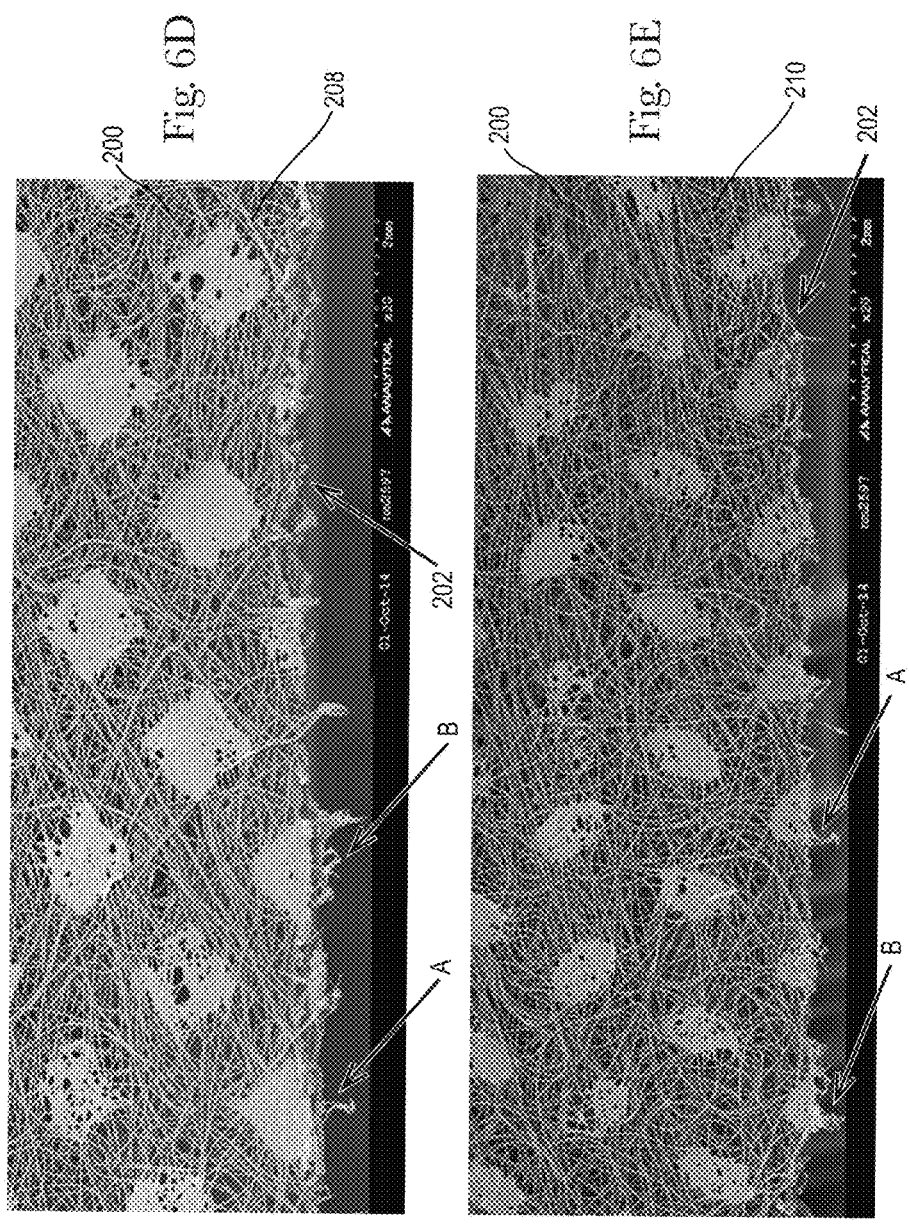

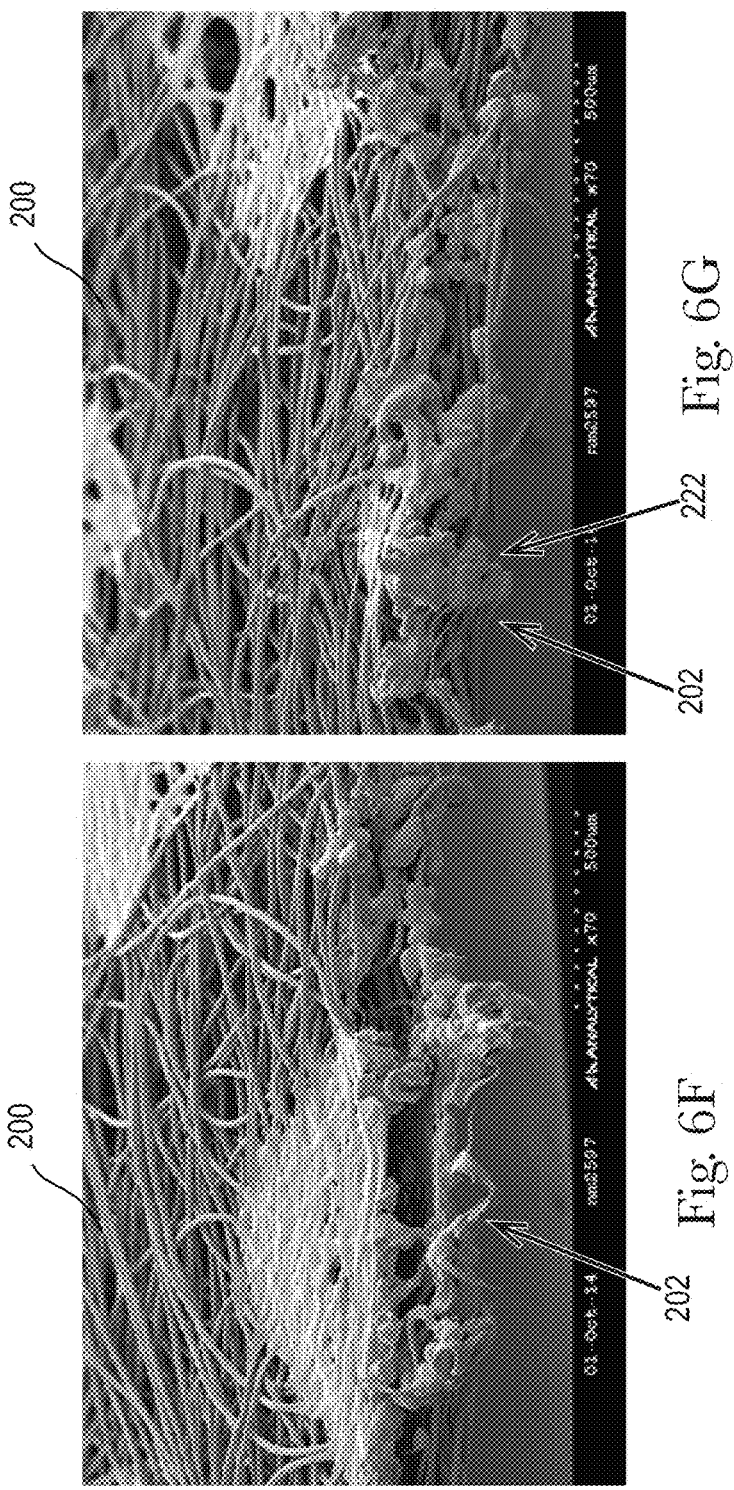

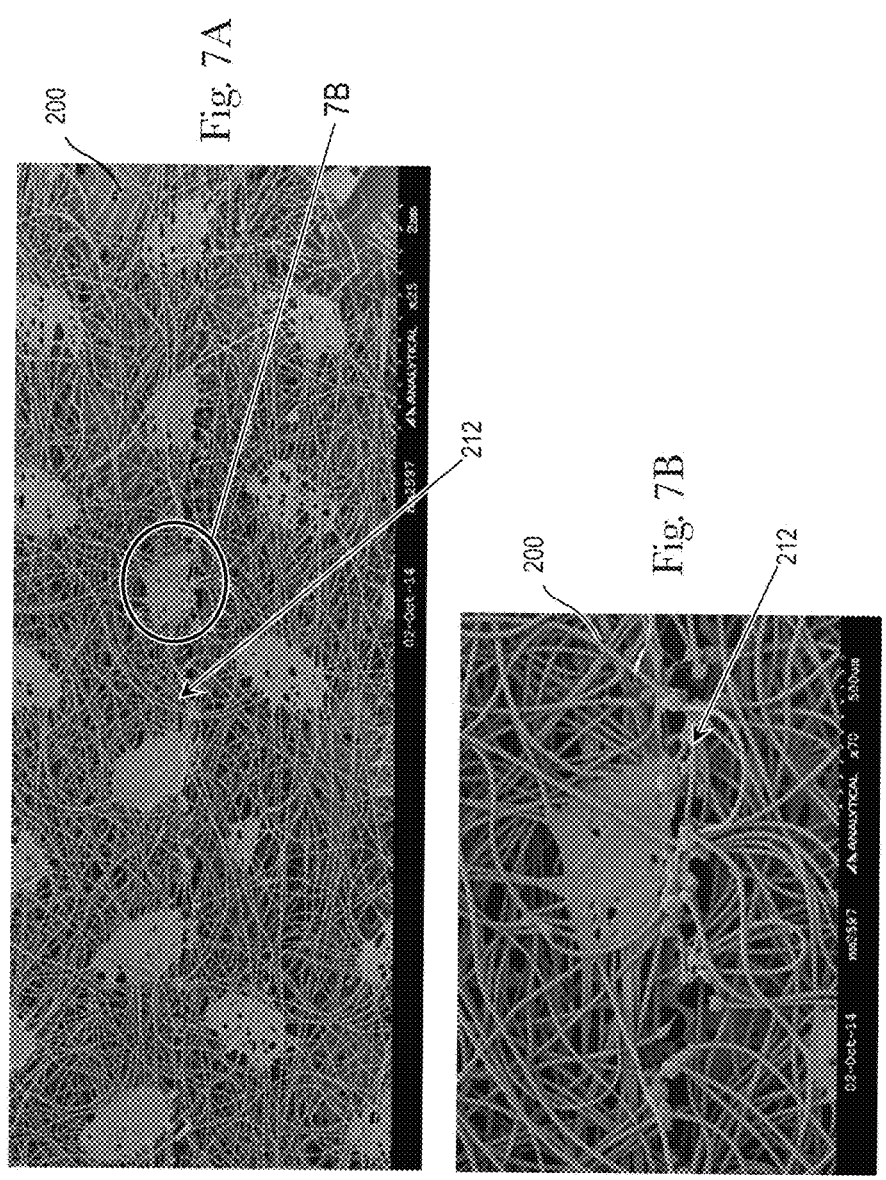

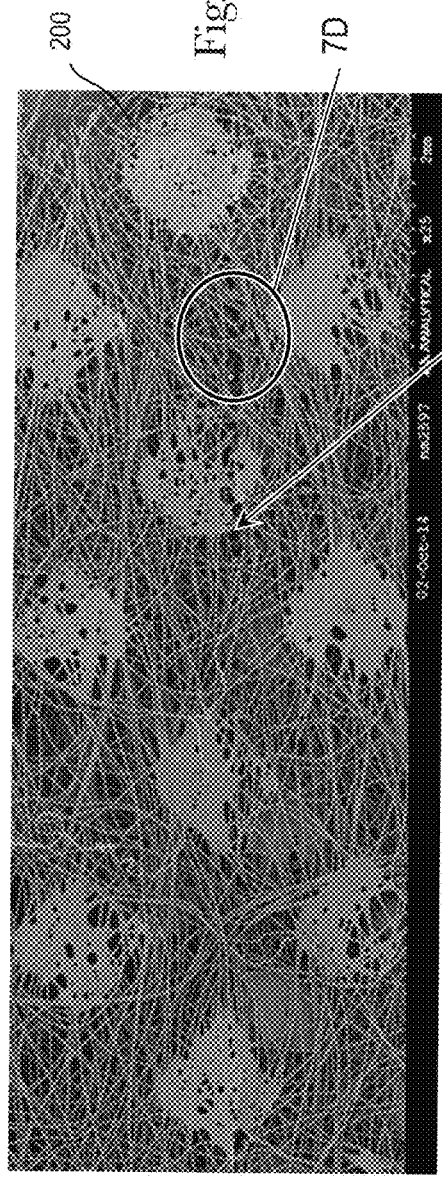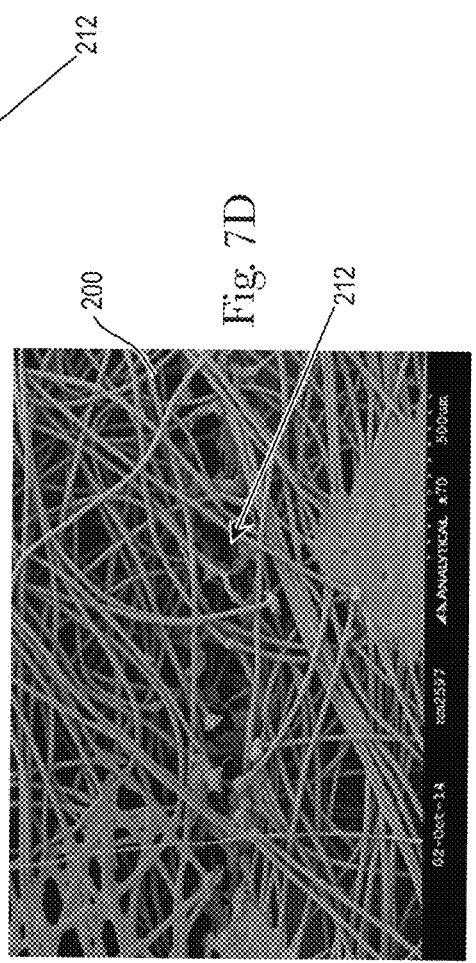

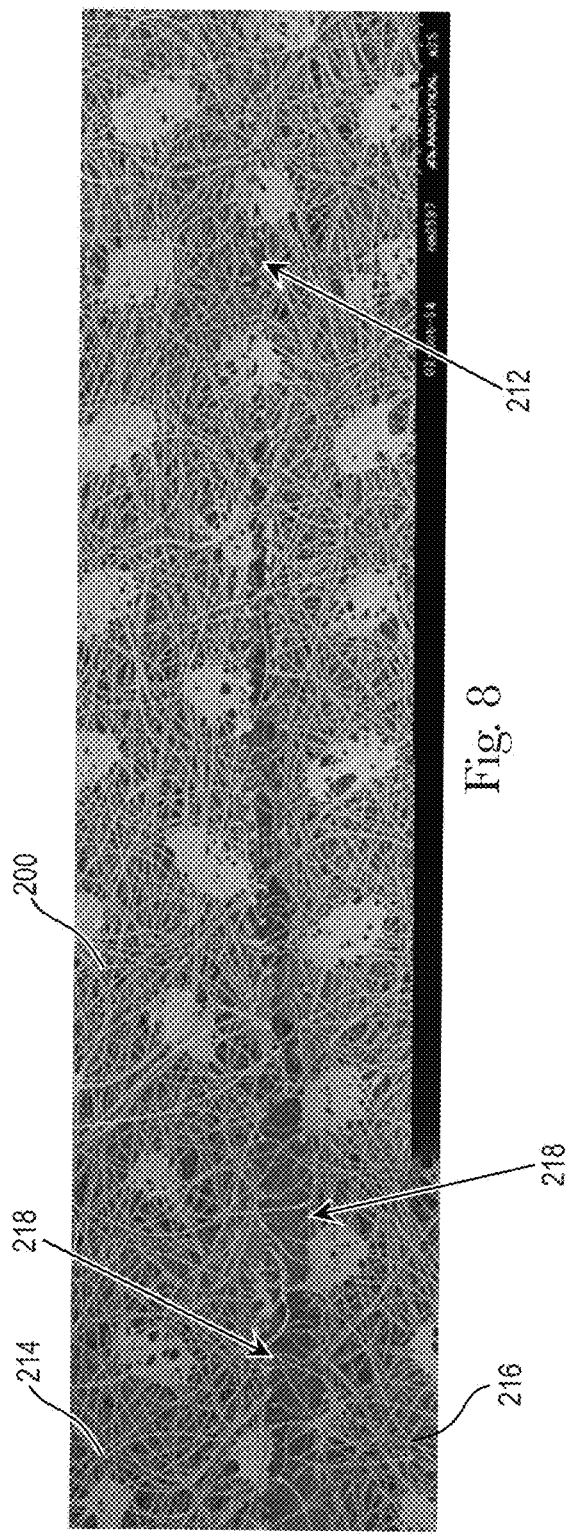

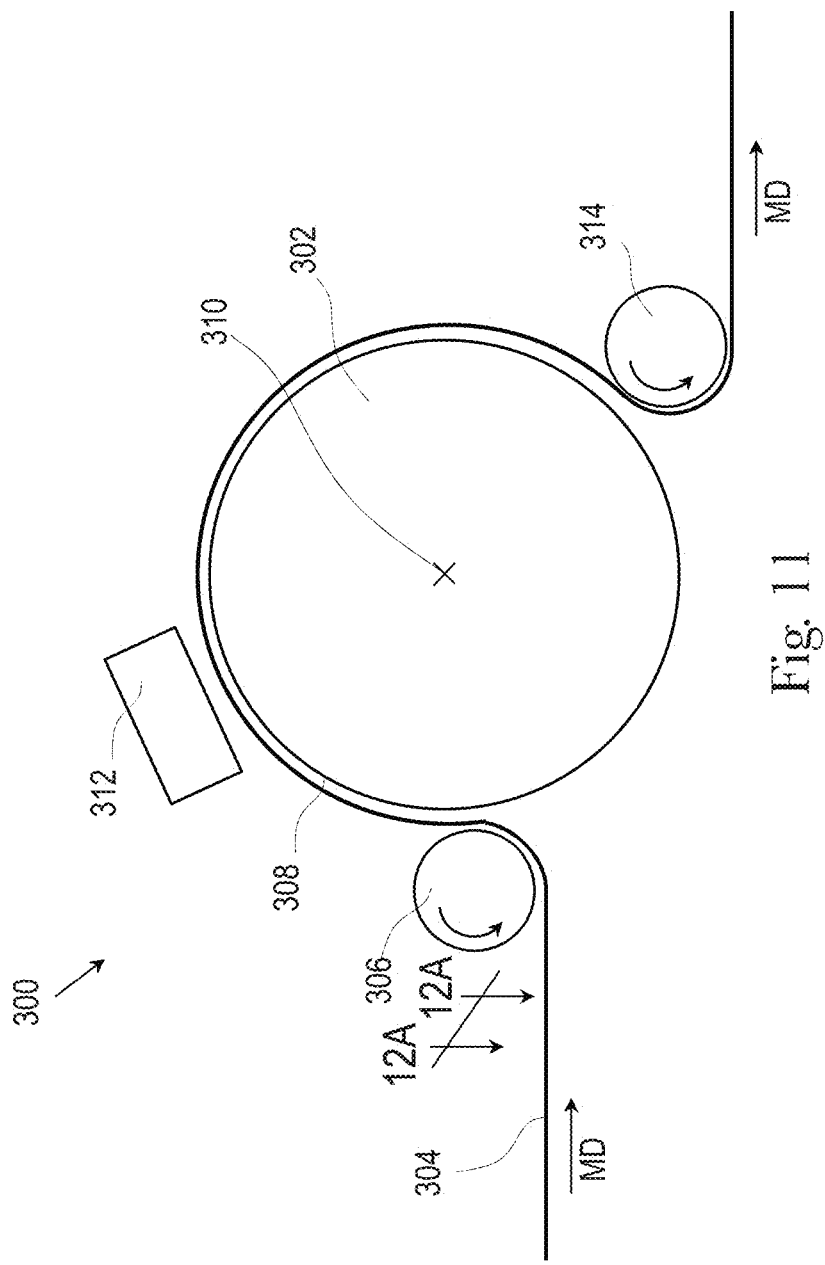

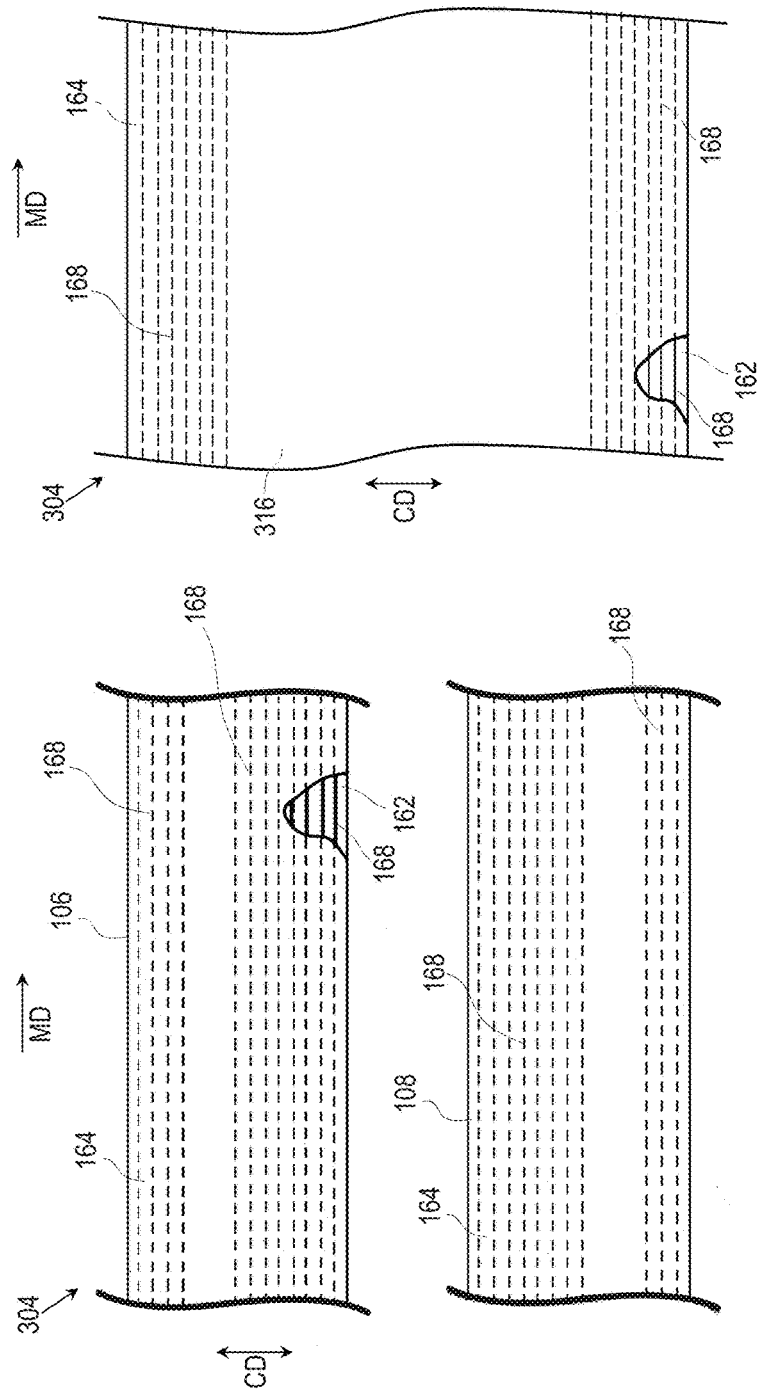

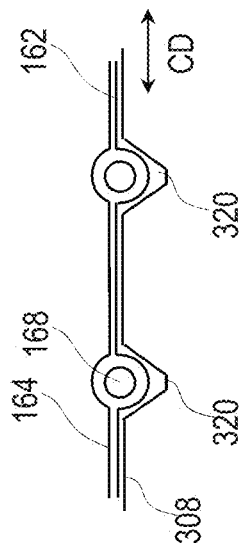
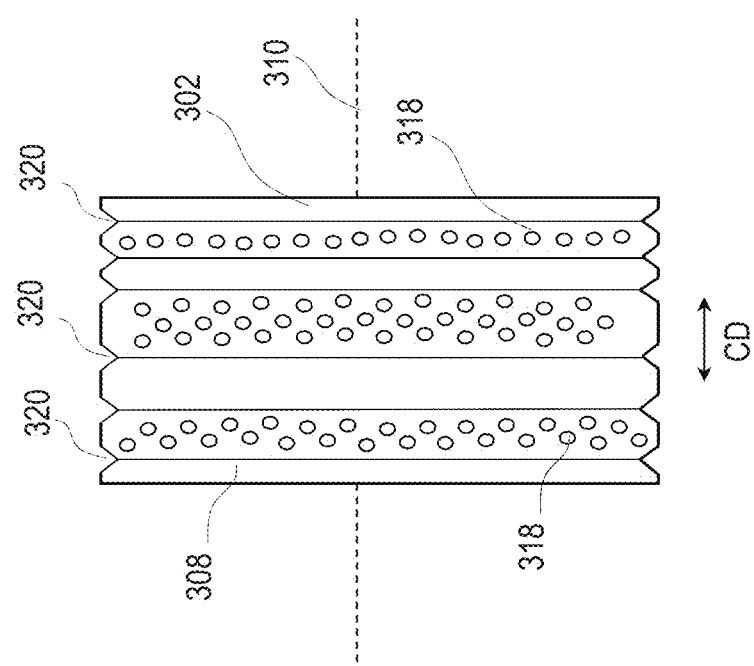

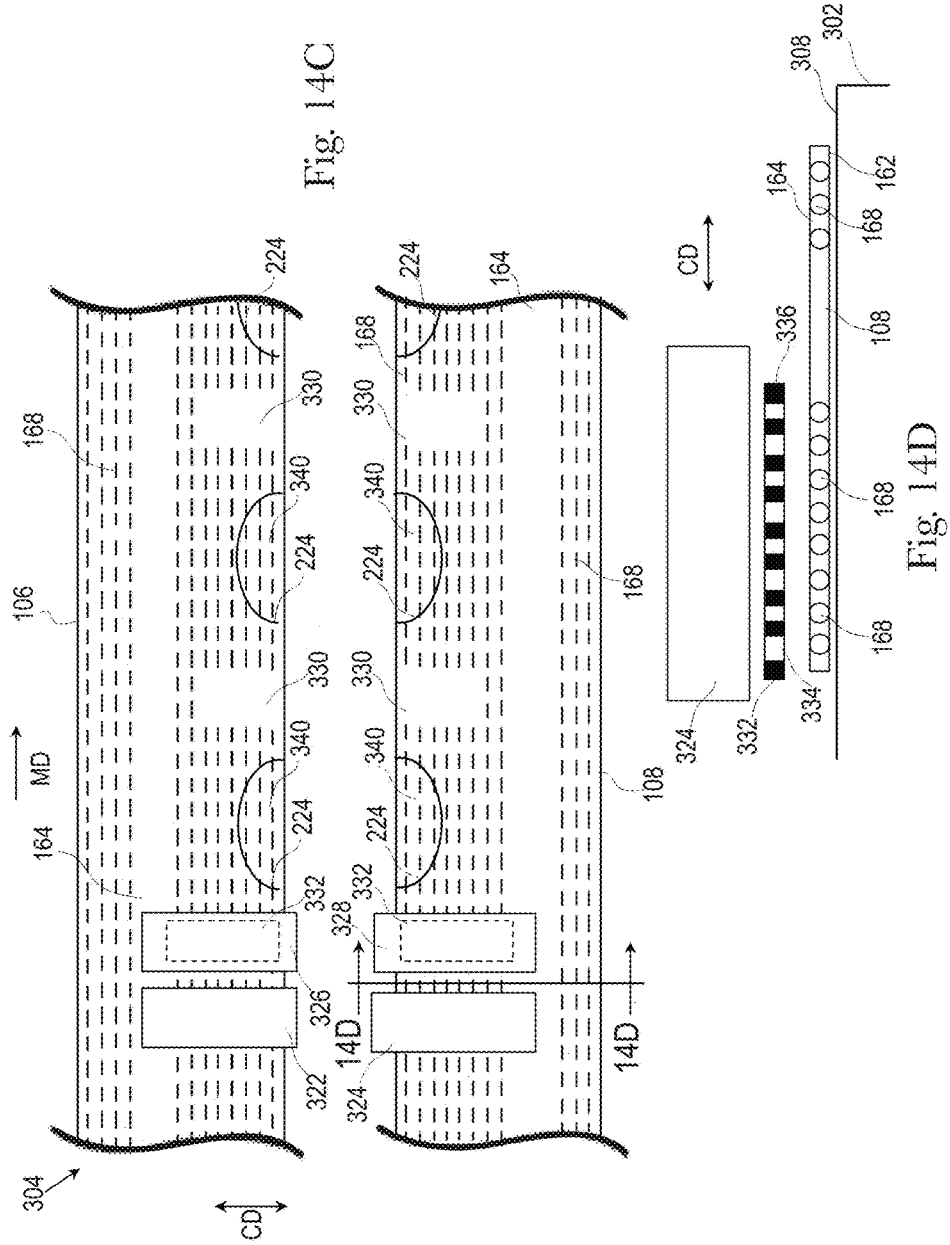

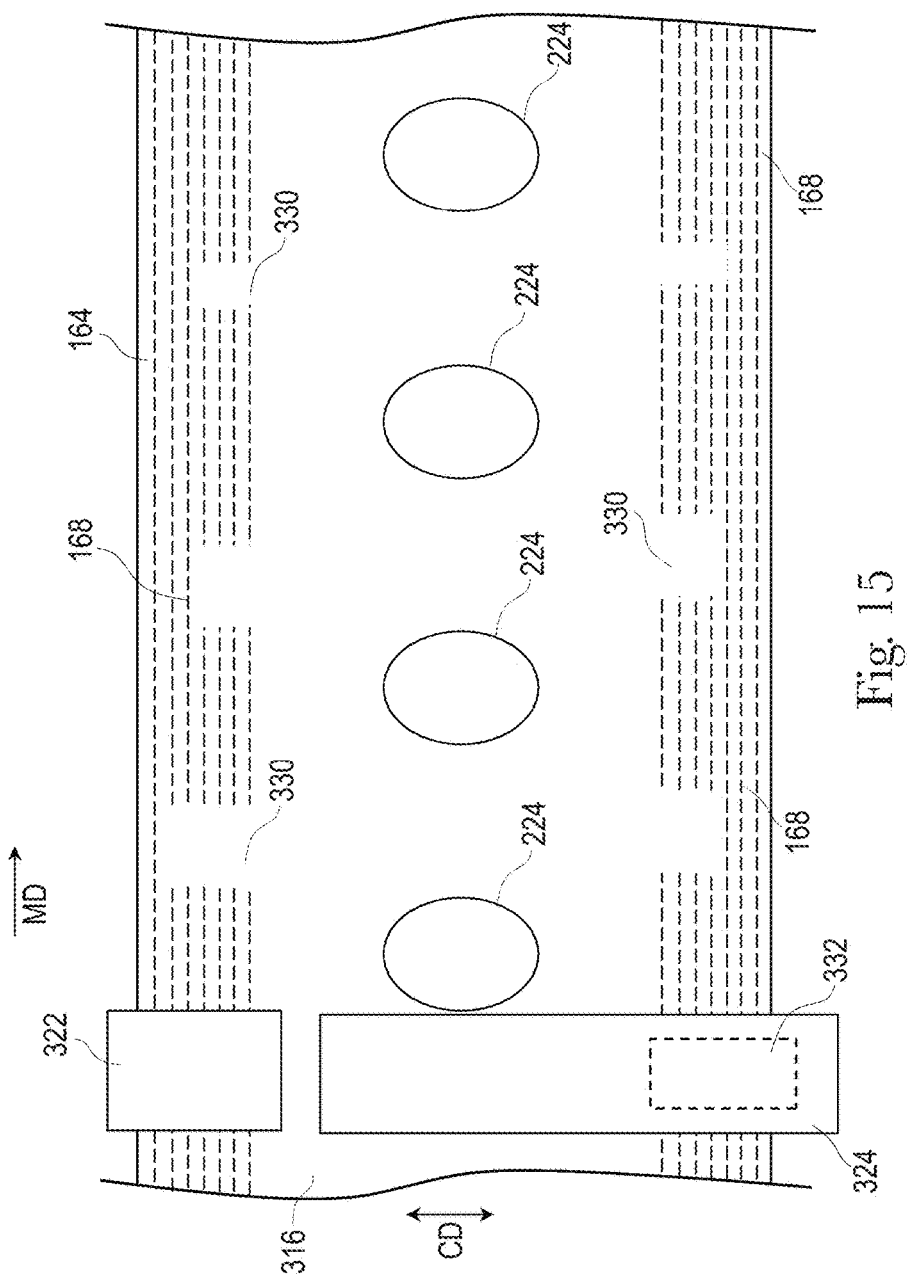

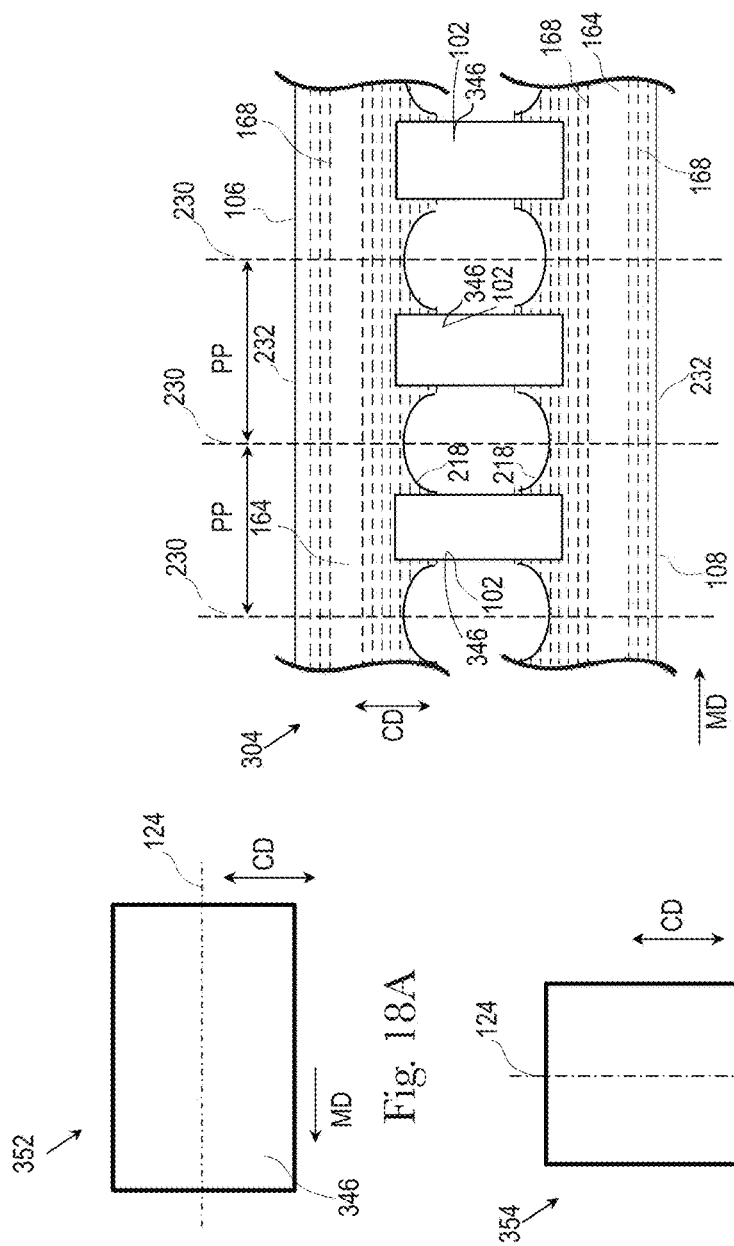
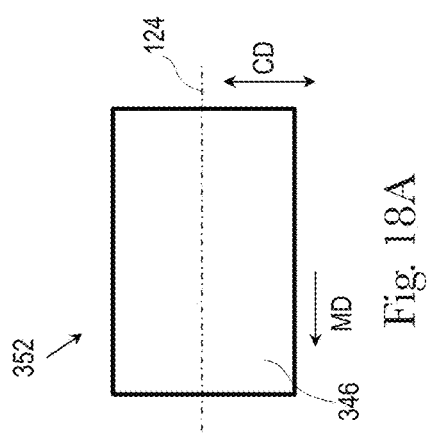
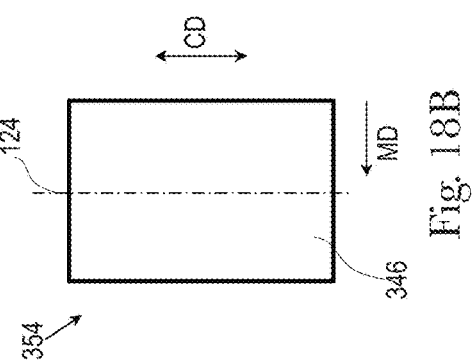

PROCESS AND APPARATUS FOR MANUFACTURING AN ABSORBENT ARTICLE USING A LASER SOURCE

CROSS REFERENCE TO RELATED APPLICATIONS

This application claims the benefit of U.S. Provisional Application No. 62/076,513 filed on Nov. 7, 2014, which is herein incorporated herein by reference.

FIELD OF THE INVENTION

The present disclosure relates to apparatuses and methods for manufacturing absorbent articles, and more particularly, methods and apparatuses for manufacturing absorbent articles using a laser source to create a line of weakness.

BACKGROUND OF THE INVENTION

Along an assembly line, various types of articles, such as for example, diapers and other absorbent articles, may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheet, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

Various methods and apparatuses may be used for attaching different components to the advancing web and/or otherwise modify the advancing web. For example, some production operations are configured to construct elastic laminates including elastics bonded with the one or more substrates advancing in a machine direction. The operations may be further configured to cut and/or otherwise deactivate discrete lengths of the elastics. In some operations, an elastic laminate may advance through a cutting station that cuts the elastic in the advancing laminate. However, some current configurations have certain drawbacks. For example, some present cutting apparatuses may cause unintended damage to the elastic laminate, such as by severing the substrate while cutting the elastic. In addition, the blades on some current cutting apparatuses may be susceptible to wear after relatively short operating periods. Such blade wear may manifest itself in inconsistent elastic cutting. Further, a blade may be re-sharpened only a certain number of times before the cutting device, as a whole, needs to be replaced, and there are costs associated with maintaining worn cutting devices and ultimately replacing the cutting device. Thus, it may be relatively expensive to maintain and replace cutting devices.

Similar to the above, other production operations are configured to advance substrates in a machine direction and cut and/or remove trim from the advancing substrates. In some operations, a substrate may advance through a cutting station that cuts trim from the advancing substrate. The trim may subsequently be diverted from the advancing substrate and into a vacuum chute or other similar apparatus for disposal. In some instances after passing through the cutting nip, the trim may remain attached to the advancing substrate by uncut fibers after passing through the cutting station. As such, the trim may undesirably continue to advance with the substrate along the assembly line negatively affecting further processing Consequently, it would be beneficial to provide methods and apparatuses that are configured to provide relatively consistent cutting of substrates and/or elastics without excessive and/or unintentional damage to the substrate, and that are configured to accurately remove trim from the advancing substrates. It would also be beneficial to provide methods and apparatuses that are not susceptible to blade wear.

SUMMARY OF THE INVENTION

The present disclosure relates to methods and apparatuses for assembling absorbent articles, and more particularly, methods and apparatuses for using a laser source to cut and/or impart one or more lines of weakness. In some embodiments, a method for manufacturing an absorbent article includes the steps of: advancing a discrete component on a carrier member; rotating a transfer member about a first axis of rotation, wherein the transfer member comprises a substantially flat transfer surface; accepting the discrete article on the substantially flat transfer surface; advancing a first substrate, a second substrate, and one or more elastic strands toward a process member; receiving the second substrate on an outer circumferential surface of the process member, wherein the process member rotates about a longitudinal axis of rotation; attaching at least a portion of the one or more elastic strands to the first substrate; disposing the second substrate on at least a portion of the one or more elastic strands and the first substrate to form a belt assembly; advancing the belt assembly to a first laser source, where the first laser source imparts a line of weakness on the belt assembly; advancing the belt assembly to the second laser source, wherein the second laser source severs a portion of the one or more elastic strands forming a gap; and positioning the discrete component on a portion of the belt assembly.

In some embodiments, a method for manufacturing an absorbent article includes the steps of: advancing a belt assembly around a portion of a first guide roller, wherein the belt assembly comprises an outer substrate, an inner substrate, and one or more elastic strands disposed between the outer substrate and the inner substrate; disposing the outer substrate of the belt assembly on an outer circumferential surface of a process member; rotating the process member about a longitudinal axis of rotation; advancing the belt assembly to a first laser source, wherein the first laser source imparts a line of weakness into the belt assembly; advancing the belt assembly to a trim removal member, wherein the trim removal member separates the line of weakness forming a trim portion and a separation edge; advancing the belt assembly to a second laser source, wherein the second laser source severs a portion of the one or more elastic strands forming a gap; advancing a discrete component toward the process member; orienting the discrete component; and positioning the discrete component on a portion of the belt assembly.

In some embodiments, a method for manufacturing an absorbent article includes the steps of: advancing a belt assembly in a machine direction, wherein the belt assembly comprises an outer layer, an inner layer, and one or more elastic strands disposed between the outer layer and the inner layer; disposing the outer layer of the belt assembly on an outer circumferential surface of a process member; rotating the process member about a longitudinal axis of rotation; advancing the belt assembly to a first laser source, wherein the first laser source imparts a line of weakness into the belt assembly; advancing the belt assembly to a cutting member, wherein the cutting member severs a portion of the one or more elastic strands forming a gap; and advancing the belt assembly to a trim removal member, wherein the trim removal member separates the line of weakness forming a trim portion and a separation edge.

BRIEF DESCRIPTION OF THE DRAWINGS

FIG. 2 is a partially cut away plan view of the diaper pant shown in FIG. 1;

FIG. 3A is a cross-sectional view of the diaper pant of FIG. 2 taken along line 3A-3A;

FIG. 3B is a cross-sectional view of the diaper pant of FIG. 2 taken along line 3B-3B;

FIG. 6D is a photograph of a portion of a cut edge of a substrate;

FIG. 6E is a photograph of a portion of a cut edge of a substrate;

FIG. 6F is a photograph of a portion of a cut edge of a substrate;

FIG. 6G is a photograph of a portion of a cut edge of a substrate;

FIG. 7A is a photograph of a portion of a substrate including line of weakness;

FIG. 7B is a photograph of a portion of a substrate including line of weakness;

FIG. 7C is a photograph of a portion of a substrate including line of weakness;

FIG. 7D is a photograph of a portion of a substrate including a line of weakness;

FIG. 8 is a photograph of a portion of a substrate including line of weakness;

FIG. 11 is a schematic representation of an apparatus that imparts a line of weakness into a substrate in accordance with one non-limiting embodiment of the present disclosure;

FIG. 12A is a top view of a belt assembly in accordance with one non-limiting embodiment of the present disclosure;

FIG. 12B is a top view of a belt assembly in accordance with one non-limiting embodiment of the present disclosure;

FIG. 13A is a side view of a process member in accordance with one non-limiting embodiment of the present disclosure;

FIG. 13B is a partial side view of a belt assembly disposed on a process member in accordance with one non-limiting embodiment of the present disclosure;

FIG. 14C is a top view of a belt assembly including a discrete line of weakness and a gap in accordance with one non-limiting embodiment of the present disclosure;

FIG. 14D is a schematic representation of a side view of a mask positioned between a laser source and a portion of the belt assembly disposed on a process member in accordance with one non-limiting embodiment of the present disclosure;

FIG. 15 is a top view of a belt assembly including a discrete line of weakness and a gap in accordance with one non-limiting embodiment of the present disclosure;

FIG. 18A is a top view of a discrete component in a first orientation in accordance with one non-limiting embodiment of the present disclosure;

FIG. 18B is a top view of a discrete component in a second orientation in accordance with one non-limiting embodiment of the present disclosure;

FIG. 18C is a top view of a belt assembly including a discrete component in accordance with one non-limiting embodiment of the present disclosure;

DETAILED DESCRIPTION OF THE INVENTION

Figure 1:
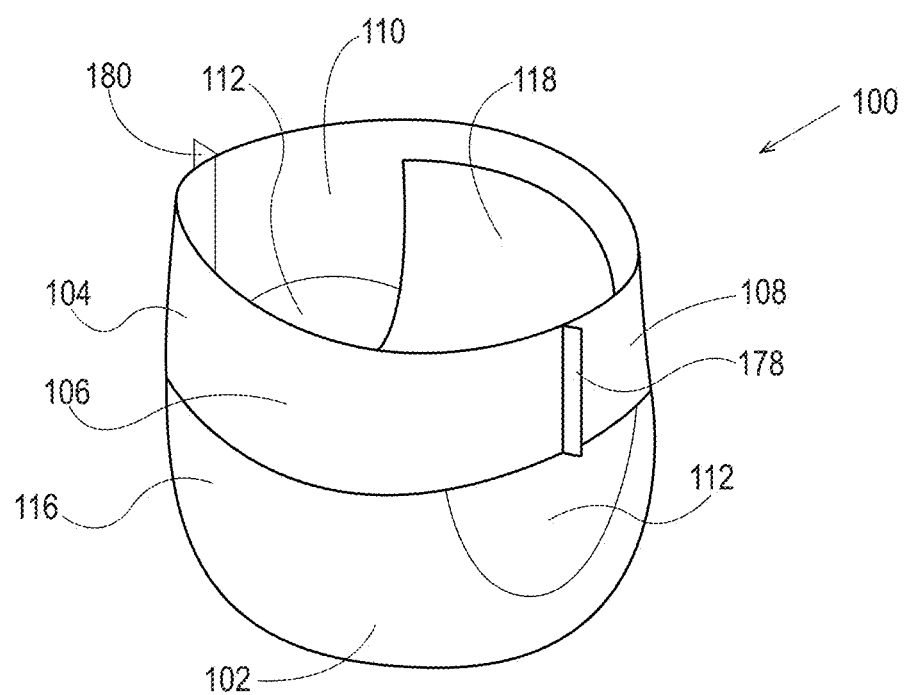
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after an initial use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

The term "extensible" as used herein refers to any material that upon application of a biasing force, can stretch to an elongated length of at least about 110% of its relaxed, original length (i.e. can stretch to 10%), without rupture or breakage, and upon release of the applied force, shows little recovery, less than about 40% of its elongation.

The terms "activating", "activation" or "mechanical activation" refer to the process of making a substrate, or an elastomeric laminate more extensible than it was prior to the process. "Live stretch" includes stretching elastic and bonding the stretched elastic to a substrate. After bonding, the stretched elastic is released causing it to contract, resulting in a "corrugated" substrate. The corrugated substrate can stretch as the corrugated portion is pulled to about the point that the substrate reaches at least one original flat dimension. However, if the substrate is also elastic, then the substrate can stretch beyond the relaxed length of the substrate prior to bonding with the elastic. The elastic is stretched at least 25% of its relaxed length when it is bonded to the substrate.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. ¹/₁₀ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed.

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

The term "taped diaper" refers to disposable absorbent articles having an initial front waist region and an initial rear waist region that are not fastened, pre-fastened, or connected to each other as packaged, prior to being applied to the wearer. A taped diaper may be folded about its lateral central axis with the interior of one waist region in surface to surface contact with the interior of the opposing waist region without fastening or joining the waist regions together. Example taped diapers disclosed in various suitable configurations are disclosed in U.S. Pat. Nos. 5,167,897; 5,360, 420; 5,599,335; 5,643,588; 5,674,216; 5,702,551; 5,968, 025; 6,107,537; 6,118,041; 6,153,209; 6,410,129; 6,426, 444; 6,586,652; 6,627,787; 6,617,016; 6,825,393; and 6,861,571.

The present disclosure relates to methods and apparatuses for assembling absorbent articles, and more particularly, methods and apparatuses for using a laser source to cut one or more portions of the components of the absorbent article and/or to create one or more lines of weakness in one or more portions of the components of the absorbent article.

To help provide additional context to the subsequent discussion of the process embodiments, the following provides a general description of absorbent articles in the form of diapers that may be assembled in accordance with the methods and apparatuses disclosed herein. Although the methods and apparatuses herein are discussed below in the context of manufacturing absorbent articles, it is to be appreciated that the assembly methods and apparatuses herein may be configured to manufacture various types of substrates.

Figure 4:
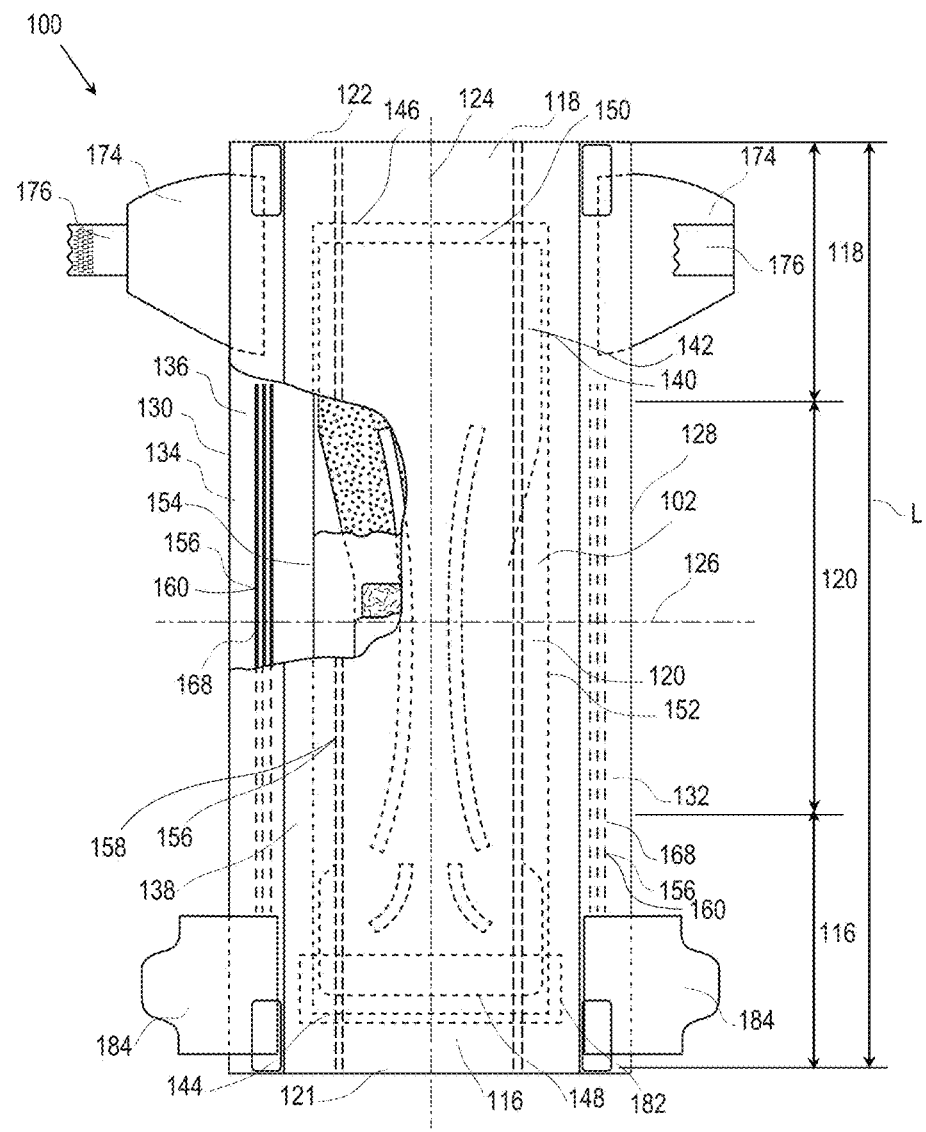
FIG. 4 is a partially cut away plan view of a diaper.

FIGS. 1, 2, and 4 illustrate an example of an absorbent article 100, such as a diaper, that may be assembled with the methods and apparatuses discussed herein. In particular, FIG. 1 shows a perspective view of an absorbent article 100 in a pre-fastened configuration, and FIG. 2 shows a plan view of the absorbent article 100 with the portion of the diaper that faces away from a wearer oriented towards the viewer. The absorbent article 100 shown in FIGS. 1 and 2 includes a chassis 102 and a ring-like elastic belt 104. As discussed below in more detail, a first belt 106 and a second belt 108, which are both elastic, are connected together to form the ring-like elastic belt 104.

With continued reference to FIG. 2, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the absorbent article 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1, 2, and 4, the absorbent article 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the absorbent article 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. When the absorbent article 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. Moreover, the crotch region 120 may be generally positioned between the legs of the wearer with the absorbent core 142 extending from the front waist region 116 through the crotch region 120 to the back waist region 118.

It is also to be appreciated that a portion or the whole of the absorbent article 100 may also be made laterally extensible. The additional extensibility may help allow the absorbent article 100 to conform to the body of a wearer during movement by the wearer. The additional extensibility may also help, for example, allow the diaper 100, including a chassis 102 having a particular size before extension, to extend in the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also include a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also include an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the absorbent article 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets, and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

The absorbent article 100 may also include an absorbent assembly 140 that is joined to the chassis 102. As shown in FIGS. 2 and 4, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core may comprise a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

The absorbent article 100 may also include elasticized leg cuffs 156. It is to be appreciated that the leg cuffs 156 may be and are sometimes also referred to as leg bands, side flaps, barrier cuffs, elastic cuffs, or gasketing cuffs. The elasticized leg cuffs 156 may be configured in various ways to help reduce the leakage of body exudates in the leg regions. For example, in some embodiments, a gasketing leg cuff 160 may be positioned adjacent to the side edge 130, 128 of the chassis 102 and a barrier leg cuff 158 may be positioned between a gasketing leg cuff 160 and the longitudinal axis 124 of the absorbent article 100. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730A1; and U.S. Patent Publication No. 2013/0255865A1.

As mentioned above, diaper pants may be manufactured with a ring-like elastic belt 104 and provided to consumers in a configuration wherein the front waist region 116 and the back waist region 118 are connected to each other and packaged, prior to being applied to the wearer. As such, the absorbent article may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; discrete strands; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

Referring to FIG. 4, in some embodiments, the absorbent article 100 may include a fastening system. The fastening system can be used to provide lateral tensions about the circumference of the absorbent article to hold the absorbent article on the wearer. The fastening system may comprise a fastener such as tape tabs, hook and loop fastening components, interlocking fasteners such as tabs and slots, buckles, buttons, snaps, and/or hermaphroditic fastening components. A landing zone 182 may be provided on the front waist region 116 for at least a portion of the fastener to be releasably attached to. Exemplary fastening systems may include those described in U.S. Pat. Nos. 3,848,594; 4,662,875; 4,846,815; 4,894,060; 4,946,527; 5,151,092; and 5,221,274.

As illustrated in FIG. 4, the absorbent article 100 may comprise front ears 184 and back ears 174. The front ears 184 and the back ears 174 may be an integral part of the chassis 102. For example, the front ears 184 and the back ears 174 may be formed from the topsheet 138 and/or the backsheet 136. Alternatively, the front ears 184 and the back ears 174 may be attached to the backsheet 136 and/or the topsheet 138. The front ears 184 and the back ears 174 may be extensible to facilitate attachment on the landing zone 182 and to maintain placement around the waist of the wearer. The back ears 174 may comprise a tab member 176. The tab member 176 may be attached to a portion of the back ears 174 to facilitate attachment to the landing zone 182.

As previously mentioned, the methods according to the present disclosure may be utilized to assemble discrete absorbent articles 100 and/or various components of absorbent articles 100, such as for example, chassis 102, elastic belts 106, 108, and/or leg cuffs 156. Although the following methods may be provided in the context of absorbent articles 100, as shown in FIGS. 1, 2, and 4, it is to be appreciated that the methods and apparatuses herein may be used with various process configurations and/or absorbent articles, such as for example, disclosed in U.S. Pat. No. 7,569,039; U.S. Patent Publication Nos. 2005/0107764A1, 2012/0061016A1, and 2012/0061015A1; 2013/0255861A1; 2013/0255862A1; 2013/0255863A1; 2013/0255864A1; and 2013/0255865A1.

As previously mentioned, the apparatuses and methods according to the present disclosure may be used to assemble absorbent articles. Various components are used to assemble the absorbent articles. Some of these components may require cutting so that the component is the proper size and/or the proper shape, for example, to be attached to other components. Most of these components, such as the topsheet and the backsheet, are made of nonwovens, as previously disclosed.

A laser source has been one method used to cut these component parts. The laser source may be used to project a laser beam at the component part, which may be, for example, an advancing substrate. The laser beam interacts with a portion of the nonwoven material of the advancing substrate resulting in the cutting of that portion of the advancing substrate. The advancing substrate separates into a first portion and a second portion. Each of the first portion and the second portion have a cut edge. The cut edge is the edge formed from the laser source causing the ablation and melting of the nonwoven material. Generally, the more power used by the laser source, the faster the nonwoven may be separated. Due to high manufacturing speeds, cutting substrates using a laser source requires a relatively large amount of power.

However, increasing the power of the laser source may result in degradation of the final cut edge. More specifically, cutting nonwoven components with the use of a laser source may create a rough feeling at the cut edge of the component part. This rough edge is due to the formation of accumulated material. The accumulation of material is due, in part, to the elastic and/or thermal deformation of the nonwoven during the separation of the nonwoven substrate. The individual fibers that are in relatively direct contact with the laser beam are ablated. However, the individual fibers of the nonwoven material along the cut edge or separation edge that do not get ablated undergo melting and/or shrinkage and subsequent cooling. During the subsequent cooling of the separated nonwoven, the fibers along the cut edge snap-back, which also may be described as roll back, resulting in an accumulation of material at the end portion of the fibers. Further, one or more fibers may join together to form a cluster of accumulated material. Generally, the greater the power used to separate the nonwoven, the larger the amount of accumulated material and/or clusters at the cut edge. This accumulated material is particularly undesirable for absorbent articles. Absorbent articles are intended to be worn or used in close contact with an individual's skin. Therefore, it is undesirable to have an absorbent article that is perceived to be rough and/or coarse, which may also result in irritation of the wearer's skin.

It is also to be appreciated that at least a portion of the snap-back, also referred to as roll back, may be due to the processes used to form the nonwoven substrate. The individual fibers used to form the nonwoven substrate may be made by an extrusion process. An extruder forces the individual fibers through a tubular structure resulting in the individual fibers being under some tension. As the fibers are laid down to form the nonwoven substrate, the individual fibers are still under a relative amount of tension. However, when the laser source acts on the individual fibers to separate them, the tension in the individual fibers is release when the individual fiber is separated causing the individual fiber to want to relax. This release of tension and relaxation of the individual fiber may contribute to the accumulation of material at the end of individual fiber that has undergone separation by the laser source. The tension in the individual fiber may only be one or numerous factors that contribute to the accumulation of material at the end of the individual fiber.

Figure 5:
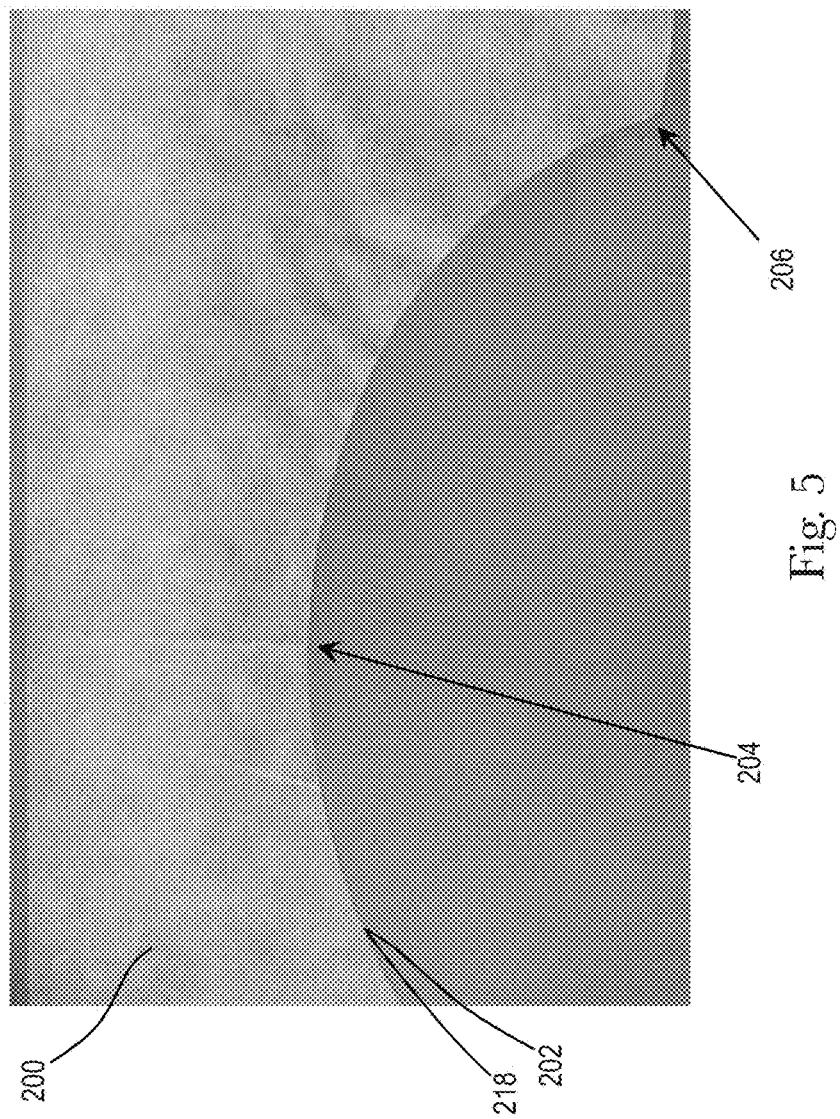
FIG. 5 is a photograph of a portion of a substrate.

FIG. 5 illustrates a nonwoven substrate 200 including a first layer and a second layer of nonwoven material that has undergone cutting by a laser source or has undergone separating after a line of weakness has been imparted by a laser source. Using a laser source to cut, also referred herein as sever, the substrate 200 in comparison to using the laser source to impart a line of weakness to the substrate and later separate the substrate, results in the edge having relatively different characteristics. As described below, a separation edge may be preferred over a cut edge. It is to be appreciated that a laser source severs or cuts the substrate when it alone separates the substrate into a first portion and a second portion along the cut edge. A laser source imparts a line of weakness when the laser source acts on the substrate resulting in the separation of some but not all of the fibers of the nonwoven and a subsequent force may be applied to separate the substrate into a first portion and a second portion.

Figure 6A:
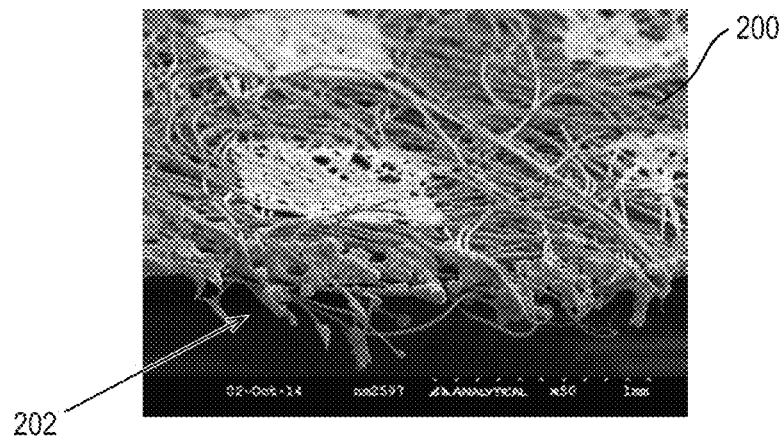
FIG. 6A is a photograph of a portion of a cut edge of a substrate.
Figure 6B:
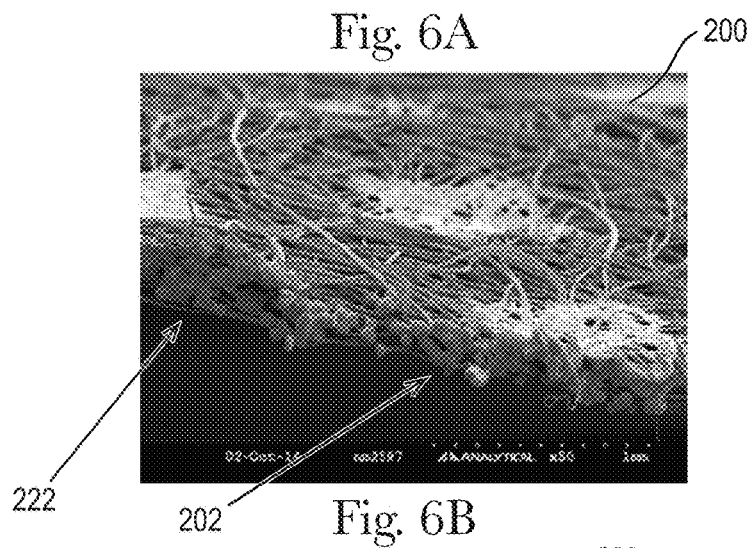
FIG. 6B is a photograph of a portion of a cut edge of a substrate.
Figure 6C:
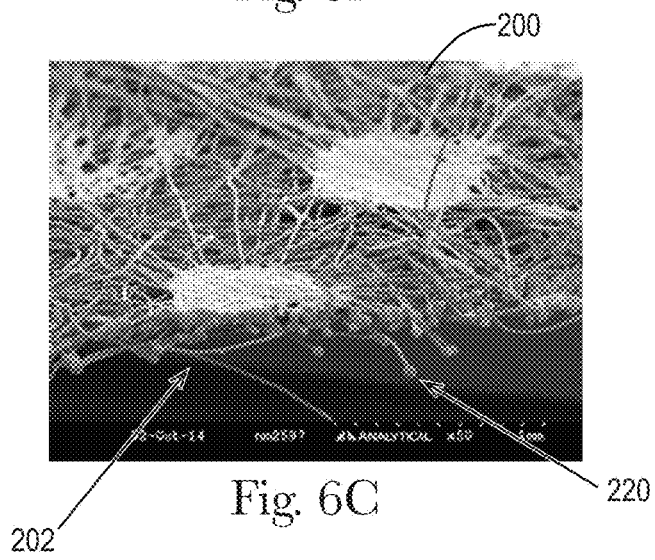
FIG. 6C is a photograph of a portion of a cut edge of a substrate.

The following is a discussion of examples wherein a substrate is cut and the results thereof. The substrate 200 is cut along the cut edge 202, which is illustrated in FIG. 5. The cut edge 202 may include a center portion 204 and an edge portion 206. In this example embodiment, the laser source was operated at 60% of its total power capacity. FIGS. 6A-6H illustrate the characteristics of the cut edge 202 after the substrate 200 was cut with a laser source operating at 60% of its total power capacity. It is to be appreciated that the laser source may be operated at various levels of total power output. FIG. 6A is a side view of the substrate 200 at the center portion 204. FIGS. 6B and 6C illustrate the area to the left and right of the edge portion 206. Further, FIGS. 6D and 6E illustrate a first surface 208 of the substrate 200 and a second surface 210 of the substrate 200. The arrows in FIGS. 6D and 6E indicate the same area, area A and area B. Further still, FIGS. 6F and 6G illustrate two additional side view of the cut edge 202. As illustrated in FIGS. 6A-6G, the fibers of the nonwoven material have accumulated material 220 at the end portions and/or along the cut edge. Further, the accumulated material 220 at the end portion of the individual fibers has joined together with the accumulated material 220 of other fibers to form a cluster 222 of accumulated material. This accumulated material 220 and clusters 222 of accumulated material makes that cut edge feel rough and/or coarse.

In comparison to the aforementioned, it is desirable to have component parts, such as substrates, that are considered to be soft, smooth, and/or non-irritating for use in absorbent articles. Thus, to solve the aforementioned problems, a laser source may be used to impart a line of weakness into the nonwoven substrate 200 rather than to cut through or sever the nonwoven substrate. The line of weakness 212 does not separate the nonwoven substrate 200. After the laser source imparts a line of weakness, a number of nonwoven fibers remain connected. These fibers keep the substrate from separating, and an additional force is required to separate the nonwoven substrate into a first portion and a second portion.

In this example embodiment, the laser source was operated at 25% of its total power capacity. FIGS. 7A-7D, 8, 9A-9B, and 10A-10B illustrate the characteristics of the separation edge 204 after a laser source operating at 25% of its total power capacity imparts a line of weakness into the substrate 200. It is to be appreciated that the laser source may be operated at various levels of total power output.

Figure 9B:
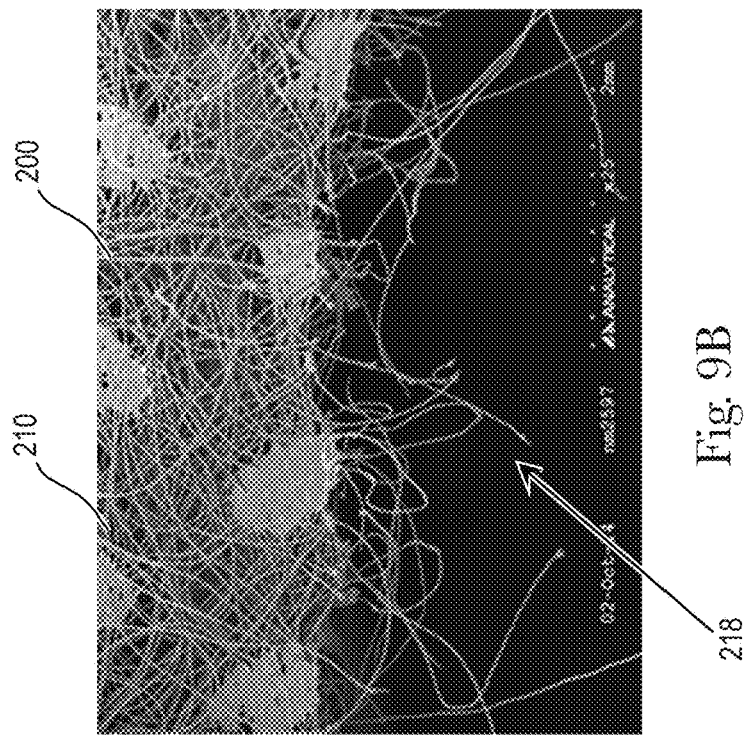
FIG. 9B is a photograph of a portion of a substrate including a separation edge.
Figure 9A:
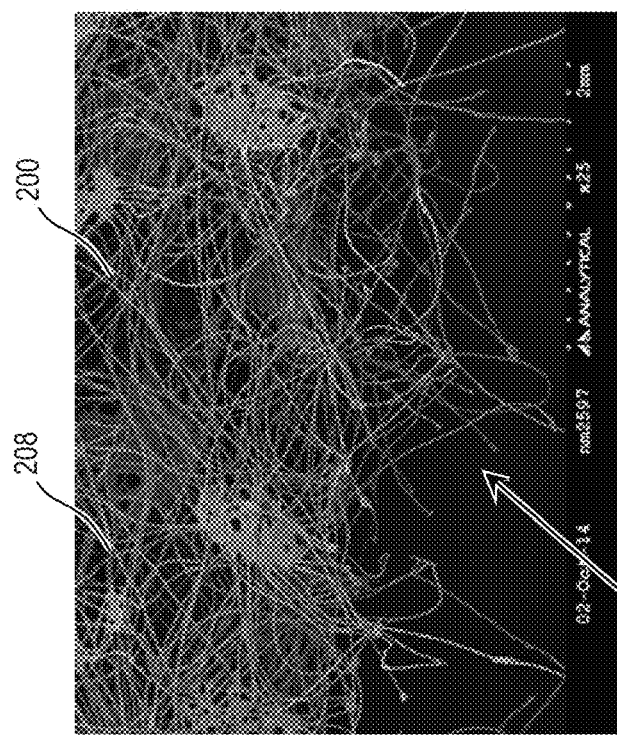
FIG. 9A is a photograph of a portion of a substrate including a separation edge.
Figure 10A:
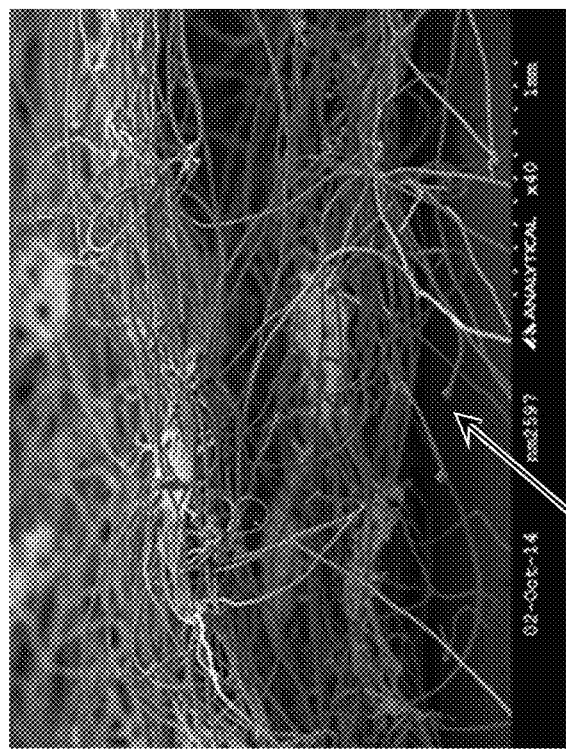
FIG. 10A is a photograph of a portion of a substrate including a separation edge.
Figure 10B:
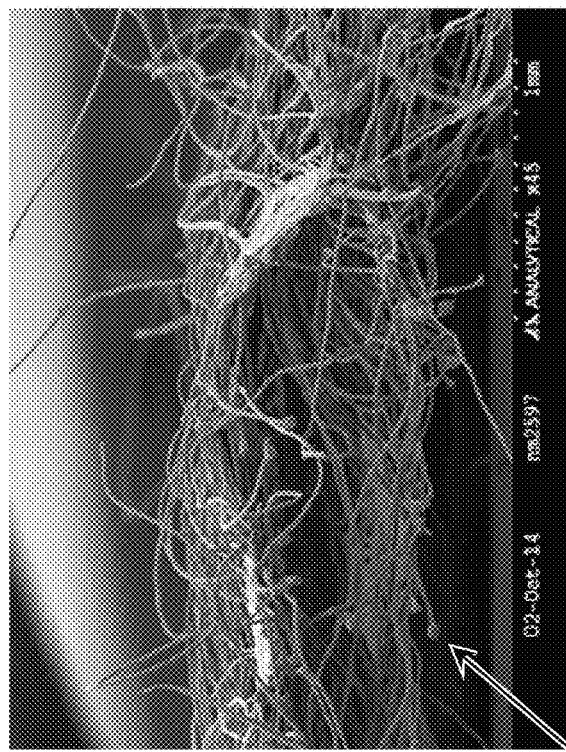
FIG. 10B is a photograph of a portion of a substrate including a separation edge.

FIGS. 7A and 7B illustrate a line of weakness 212 imparted by a laser source onto the substrate 200. FIG. 7B is a magnified view of the area indicated in FIG. 7A. Similarly, FIGS. 7C and 7D show another portion of the substrate that has a line of weakness 212. FIG. 7D is a detailed view of the portion of the line of weakness 212 as indicated in FIG. 7C. After the laser source imparts a line of weakness 212 into the substrate 200, the substrate 200 may be separated along the line of weakness 212 such that the substrate is separated into a first portion 214 and a second portion 216. FIG. 8 illustrates the separation of the substrate 200 along the line of weakness 212 creating a separation edge 218 along both the first portion 214 and the second portion 216. FIGS. 9A and 9B illustrate a first surface 208 and a second surface 210 of a portion of the substrate 200 after separation along the separation edge 218. FIGS. 10A and 10B illustrate a portion of the separation edge 218.

As evidenced by the Figures, the separation edge 218 includes less material accumulation than the cut edge 202, as shown in FIGS. 6A-6G. The reduction in material accumulation leads to the separation edge 218 being perceived as soft and/or smooth. Further, the separated edge 218, as evidence by the Figures, has a greater number of fibers that have been loosened during separation at the separation edge 218. These loosened fibers also may contribute to the softer and/or smoother feel of the substrate 200 at the separation edge 218.

The present disclosure relates to a method and apparatus to overcome the aforementioned deficiencies while utilizing a laser source, and to manufacture a substrate and/or other component parts that are perceived to be softer and/or smoother as compared to similar substrate and/or other component parts that have undergone cutting by a laser source.

FIG. 11 illustrates an exemplary schematic representation of an apparatus 300 that may be used to manufacture an absorbent article 100, as previously described. The apparatus 300 may include a process member 302. The process member 302 may rotate about a longitudinal axis of rotation 310. Further, the process member 302 may be configured to receive a belt assembly 304. It is to be appreciated that a belt assembly is used to describe the process and apparatus herein, but any laminate or multiple layer substrate may be used in the process and apparatus discussed herein. The belt assembly 304 may advance in a machine direction MD toward the process member 302. A first guide roller 306 may aid in the transfer of the belt assembly 304 onto an outer circumferential surface 308 of the process member 302. The outer circumferential surface 308 of the process member 302 may include one or more apertures, as illustrated in FIG. 13A. A vacuum source, not shown, may be in fluid communication with the one or more apertures. The vacuum source allows fluid to be circulated through the one or more apertures toward the longitudinal axis of rotation 310. The movement of fluid may result in the belt assembly 304 being forced toward the outer circumferential surface 308 of the process member 302. The process member 302 may rotate about the longitudinal axis of rotation 310 causing the belt assembly 304 to advance toward a laser source 312. The laser source 312 may be used to impart a discrete line of weakness into the belt assembly 304 or to impart a continuous line of weakness into the belt assembly 304. The belt assembly 304 having at least one of a continuous line of weakness and a discrete line of weakness may advance to additional processes such as separating the discrete trim portion and/or the continuous trim portion from the belt assembly 304 and/or adding additional components to the belt assembly 304. A second guide roller 314 may be used to advance the belt assembly 304 to these subsequent processes and/or to aid in the subsequent processes. This process and apparatus will be described in more detail herein.

As previously stated, a belt assembly 304 may be advanced toward the process member 302. The belt assembly 304 may include a first belt 106 and a second belt 108, as illustrated in FIG. 12A. The first belt 106 and the second belt 108 may be spaced such that an absorbent core or other discrete component may be disposed across a portion of the first belt 106 and the second belt 108. The first belt 106 and the second belt 108 may each include an outer layer 162, an inner layer 164 disposed in facing relationship with the outer layer 162, and elastic strands 168 disposed between the outer layer 162 and the inner layer 164. The elastic strands 168 may be stretched in the machine direction MD and bonded with the first substrate layer 162 and/or the second substrate layer 164. More particularly, the elastic strands 168 may be continuously bonded with the first substrate layer 164 and/or the second substrate layer 162 with adhesive along the machine direction MD and/or the elastic strands 168 may be intermittently bonded with the first substrate layer 162 and/or the second substrate layer 164 with adhesive along the machine direction MD. Thus, the elastic strands 168 may include non-bonded regions along the machine direction MD. The elastic strands are not bonded to either of the first substrate 162 or the second substrate 164 in the non-bonded region. It is to be appreciated that adhesive may also be applied to the first and second substrates 162, 164 between the elastic strands 168.

In some embodiments, as illustrated in FIG. 12B, the belt assembly 304 may include a unitary, body substrate 316. The body substrate 316 may include an outer layer 162, an inner layer 164 disposed in facing relationship with the outer layer 162, and one or more elastics 168 disposed between the outer layer 162 and the inner layer 164.

The belt assembly 304 may advance on to the outer circumferential surface 308 of the process member 302, as illustrate in FIG. 11. The belt assembly 304 may be disposed on the process member 302 such that either the outer layer 162 or the inner layer 164 of the belt assembly 304 is disposed on the outer circumferential surface 308. More specifically, either a surface of at least one of the outer layer 162 and the inner layer 164 may be disposed on the outer circumferential surface 308. It is to be appreciated that the outer layer 162 and the inner layer 164 may each be made up of one or more layers that have different properties, such as the type of fiber, additives, and density. The properties of the outer layer 162 and the properties of the inner layer 164 may make it advantageous to have one layer or the other layer in closer proximity to, or facing relationship with, to the laser source.

It is also to be appreciated that the characteristics of the separation edge may make it advantageous to have either the outer layer 162 or the inner layer 164 in facing relationship with the laser source. More specifically, as illustrated in FIGS. 7A-7D, 9A-9B, and 10A-10B, the separation edge may still include a portion of individual fibers having accumulated material at the end. The portion of fibers having accumulated material may be greater on the layer positioned in facing relationship with the laser source or, stated differently, the layer the laser beam first encounters when acting on the substrate. Thus, the layer having a greater portion of accumulated material may be positioned on the absorbent article such that it reduces or eliminates contact with the wearer's skin, and the layer having a lesser portion of accumulated material by be positioned on the absorbent article such that it may contact the wearer's skin. Minimizing the portion of the inner layer 164 or outer layer 162 having the greater portion of accumulated material at the ends of the individual fibers may aid in the perceived softness of the layers. The process and apparatus described herein may act on either the inner layer 164 or the outer layer 162 of a substrate.

In some embodiments, the elastic strands 168 may be positioned in a certain location on the outer circumferential surface 308. Thus, the outer circumferential surface may include one or more grooves into which the elastic stands 168 may be disposed, as illustrated in FIGS. 13A and 13 B.

FIG. 13A illustrates a process member 302 including an outer circumferential surface 308. The outer circumferential surface 308 may include one or more apertures 318 configured to transfer air toward or away from the longitudinal axis of rotation 310. The one or more apertures 318 may aid in transferring the belt assembly 304 onto the outer circumferential surface 308 and to keep the belt assembly 304 in place during rotation and subsequent processing.

Further, the outer circumferential surface 308 may include one or more grooves 320. The one or more grooves may surround the outer circumferential surface 308 such that the groove extends about the axis of rotation 310. In some embodiments, all or some of the grooves may extend only partially around the axis of rotation 310. Stated another way, the grooves 320 may be placed such that there are ungrooved portions between groove portions. Further, the grooves may be spaced in the cross direction such that there is a uniform distance between each groove 320. It is also to be appreciated that the grooves 320 may be spaced in the cross direction such that there is a non-uniform distance between each groove 320, as illustrated in FIG. 13A. The grooves may be spaced in the cross direction CD such that each groove corresponds to the desired spacing of the elastic strands 168. The outer circumferential surface 308 may include any number of grooves 320 that allow the belt assembly 304 to remain in a desired position during advancement of the belt assembly 304 and/or to locate one or more of the elastic strands 168 in the belt assembly 304. For example, to locate the elastic strands 168, the outer circumferential surface 308 may include a number of grooves 320 into which the elastic strands 168 are positioned as the belt assembly 304 is transferred onto the process member 302. FIG. 13B illustrates a portion of the outer circumferential surface 308 including one or more grooves 320 into which the elastic strands 168 are positioned. It is to be appreciated that the grooves may be any shape such as semi-circular, triangular, hexagonal, trapezoidal, or any other shape that inhibits movement of the elastic strands and/or maintains the location of the elastic strands 168 about the outer circumferential surface 308.

As illustrated in FIG. 11, the process member 302 advances the belt assembly 304 to a laser source 312. The laser source 312 may be used to impart a line of weakness into the belt assembly 304. A line of weakness refers to any region or area of weakened material, and can include linear and non-linear patterns, such as curvilinear patters of weakness, or other shapes, such as circles, rectangles, or triangles. A laser source forms a line of weakness by causing some of the fibers of the nonwoven material to separate, but not causing all the fibers of the nonwoven material to separate. Thus, after the laser source acts on the belt or other substrate, the substrate remains attached at certain locations but has become detached at other locations. The power of the laser source and the properties of the substrate determine how much of the substrate remains attached after the laser source imparts the line of weakness. A line of weakness may be a discrete line of weakness or a continuous line of weakness. A discrete line of weakness may be a line that includes a first end point and a second end point within the length of two product pitches. A continuous line of weakness may be a line that continues over the length of two or more product pitches. A product pitch PP is the length of the discrete substrate after the continuous substrate is cut into discrete portions. An example of a product pitch PP is illustrated in FIG. 18C. The product pitch is measured between a first cut line and an adjacent, second cut line parallel to the edge 232 of the substrate, which may be a belt assembly 304, as illustrated in FIG. 18C.

Figure 14A:
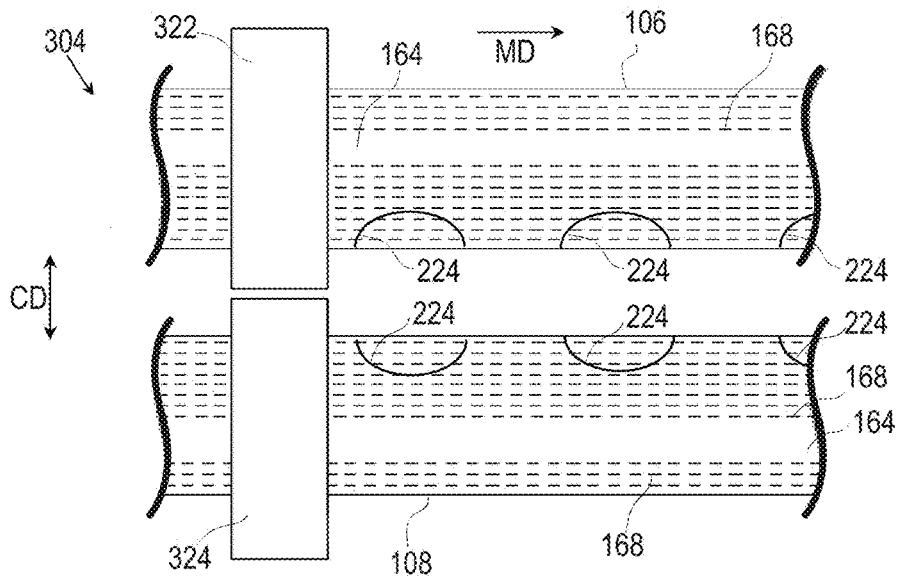
FIG. 14A is a top view of a belt assembly including a discrete line of weakness in accordance with one non-limiting embodiment of the present disclosure.

As illustrated in FIG. 14A, a laser source 312 may be used to impart a discrete line of weakness into the belt assembly. More specifically, for example, a first laser source 322 may be positioned adjacent the first belt 106 and a second laser source 324 may be positioned adjacent the second belt 108. The first laser source 322 may be used to impart discrete lines of weakness 224 into the first belt 106. The second laser source 324 may be used to impart discrete lines of weakness 224 into the second belt 108. Each of the first laser source 322 and the second laser source 324 may be powered on and off to create each discrete line of weakness. As the belt assembly 304 advances in the machine direction, the laser source 322, 324 may power on to impart a discrete line of weakness and subsequently power off until the belt assembly 304 advances to a position where a second discrete line of weakness needs to be imparted onto the belt assembly. Each discrete line of weakness 224 may have characteristics such as the line of weakness 212 described with respect to FIGS. 7A-7D, 9A-9B, and 10A-10B.

It is also to be appreciated that a discrete line of weakness may also be imparted to the substrate by a laser that remains powered on. For example, the laser source may remain powered on but may be diverted to the edge of the substrate or the laser source may be directed to the outer circumferential surface of the process member. More specifically, the laser source remain powered on while the substrate advances in the machine direction. As the substrate advances, the laser beam of the laser source may be diverted such that it imparts a discrete line or weakness and, subsequently, may be diverted again such that the laser beam is adjacent the edge of the substrate or, state another way, does not act on the substrate but, rather, is positioned over the outer circumferential surface of the process member.

The power output of the laser source 322, 324 may be adjusted while the laser source is powered on or while the laser source is powered off. For example, a first discrete line of weakness may be imparted to the belt assembly at a first power output and a second discrete line of weakness may be imparted to the belt assembly at a second power output, wherein the first power output is greater than or less than the second power output. The power of the laser source may also be adjusted while imparting a single, discrete line of weakness. More specifically, the laser source may impart a portion of the discrete line of weakness at a first power output and impart another portion of the discrete line of weakness at a second power output, which is greater than or less than the first power output. For example, a belt assembly may include a first portion including a single substrate layer and a second portion including more than one substrate layers, such as two or three substrate layers. A discrete or continuous line of weakness may be required to be imparted over both the first portion and the second portion of the belt assembly. Thus, the laser source may operate at a first power output as it imparts the line of weakness over the first portion including only a single substrate layer and the laser source may operate at a second power output, which is different than the first power output, as it imparts the line of weakness over the second portion including more than one substrate layer. The laser source may be adjusted from the first output power to the second output power while it is powered on and imparting the line of weakness into the belt assembly. The power output of the laser source may increase as the number of layers of substrate into which the line of weakness needs to be imparted increases. It is to be appreciated that there may be one or more laser sources 321 depending on the type of cut and/or line of weakness that needs to be imparted to the belt assembly 304.

Figure 14B:
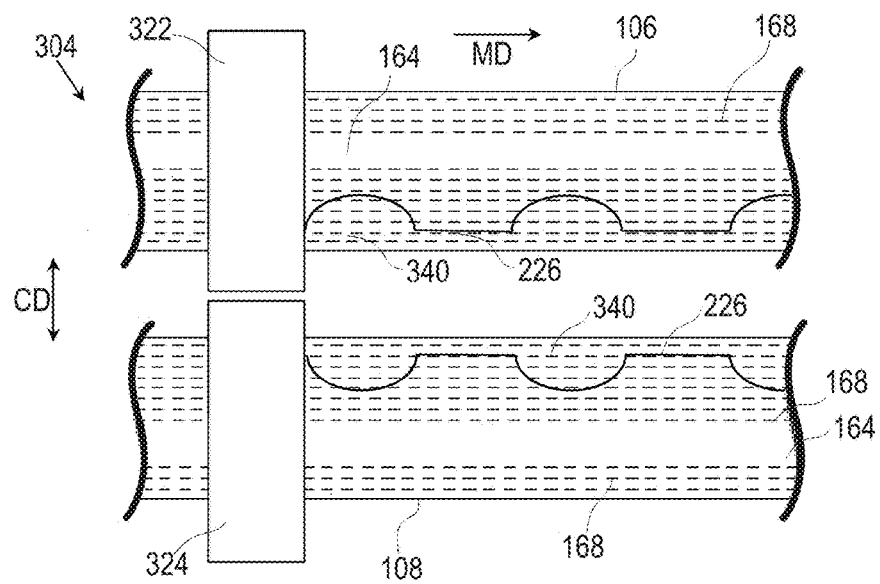
FIG. 14B is a top view of a belt assembly including a continuous line of weakness in accordance with one non-limiting embodiment of the present disclosure.

The line of weakness may be a continuous line of weakness, as illustrated in FIG. 14B. A first laser source 322 may be positioned adjacent the first belt 106 and a second laser source 324 may be positioned adjacent the second belt 108. The first laser source 322 may be used to impart a continuous line of weakness 226 into the first belt 106. The second laser source 324 may be used to impart a continuous line of weakness 226 into the second belt 108. The continuous lines of weakness 226 may have characteristics such as the line of weakness 212 described with respect to FIGS. 7A-7D, 9A-9B, and 10A-10B. It is to be appreciated that the power output of the laser source 322, 324 may be adjusted while the laser source is imparting the continuous line of weakness onto the belt assembly, as previously described. In addition, in order to ensure separation of the trim portion of the line of weakness, the power output of the laser source may need to be increased around curved or non-linear portions of the continuous line of weakness. This may cause more of the fibers in these regions to separate making it easier to separate and remove the trim from the belt assembly along the continuous line of weakness.

In some embodiments, a series of laser sources may be used, as illustrated in FIG. 14C. For example, a first laser source 322 may be used to impart a discrete line of weakness 224 into a first belt 106 and a second laser source 324 may be used to impart a discrete line of weakness 224 into a second belt 108. Further, a third laser source 326 and a fourth laser source 328 may be used to sever one or more elastic strands 168 forming a gap 330 of elastic strands 168 in the belt assembly 304. More specifically, the third laser source 326 may be used to sever one or more elastic strands 168 in the first belt 106 and the fourth laser source 328 may be used to sever one or more elastic strands 168 in the second belt 108. The elastic strands 168 may be located in the portion of the belt assembly that overlaps a discrete component or sub-assembly, such as an absorbent core, as described with reference to FIGS. 2 and 4, which may be disposed on the belt assembly 304 in a subsequent process. The elastic strands 168 may be severed in this region to prevent the belt assembly from gathering in the region of the absorbent core and/or the chassis, which are examples of component parts that may be added to the belt assembly 304. The laser source may be configured to sever any number of elastics 168. Thus, the size of the gap may differ across a belt assembly 304.

In some embodiments, the laser source may be operated in the cross direction as the belt assembly advances in the machine direction to sever the one or more elastic strands. More specifically, the laser source and/or the laser beam emitted by the laser source may be operated such that it imparts a continuous line across the portion of the elastic strands that are desired to be severed. It is to be appreciated that the laser source 312 and/or laser beam may also move in a direction at an angle to the cross direction CD. For example, the laser source 312 or laser beam may move in a substantially diagonal direction due to the movement of the belt assembly 304 in the machine direction MD. Thus, the movement of the belt assembly in the machine direction may be accounted for in the movement of the laser such that the laser source and/or laser beam moves in a diagonal direction so that the elastic strands are severed in a line extending parallel to the cross direction.

In some embodiments, a mask 332 may be used to prevent those portion of the nonwoven that do not overlap an elastic strand 168 from being affected by the laser source. The mask 332 may be positioned between the laser source 324 and the belt assembly 304, as illustrated in FIGS. 14C and 14D. The mask 332 may include transfer portions 334, which allows the laser source to interact with the substrate and the elastic strand(s), and preventative portion 336, which stops the laser source from acting on the substrate and the elastic strand(s). The mask 332 may be positioned such that the transfer portions 334 coincide with the elastic strands and the preventative portions 336 coincide with the portions of the elastic belt that do not have elastic strands. Stated another way, a laser source may continuously operate as it moves in the cross direction to sever the elastic strands 168. The mask allows the laser source to affect only certain portions of the nonwoven substrate(s), most desirably portions overlapping elastic strands 168. The mask 332 may be configured with any number of transfer portions and preventative portions. The number and design of these portions will depend, in part, on which portions of the nonwoven substrate(s) it is desirable for the laser source to affect. The mask may be moveable. The mask may be continually adjusted in one or more directions so that it may maintain alignment with the portion of the substrate that is desired to be acted on by the laser source.

In some embodiments, the laser source may be pulsed so that certain portions of the nonwoven substrate remain unaffected by the laser source. For example, the laser source may be controlled such that the laser source is powered on for a certain period of time and off for a certain period of time. The amount of the time the laser source is powered on and powered off may depend, in part, on the speed of the belt assembly advancing in the machine direction and the characteristics of the line of weakness. The amount of time that the laser source is powered on and powered off may be changed each time the laser source completes an on/off cycle. Thus, the laser source may remain powered on for a longer period of time in a first cycle and remain powered on for a shorter period of time in a subsequent cycle.

Pulsing of the laser source may also be used to impact the quality of the line of weakness or the cut. For example, pulsing the laser source may reduce the amount of heat transferred to the material in a region, thereby reducing the amount of melting of individual fibers and the clustering of adjacent fibers. Thus, pulsing may also aid in improving the softness, as perceived by the user, of the cut edge or separated edge.

Pulsing of the laser source may be used to impart both a continuous line of weakness or a discrete line of weakness. Pulsing of the laser source used to impart either a continuous line of weakness or a discrete line of weakness may result in the line of weakness having individual discrete segments of areas affected by the laser source. Thus, a discrete line of weakness may include discrete segments and a continuous line of weakness may include discrete segments when imparted by a laser source that has been pulsed.

It is to be appreciated that to use the laser source in this manner to sever one or more elastics, the location of the elastics must be known or detected. As previously described, the outer circumferential surface of the process member may include one or more grooves. Thus, each elastic strand may be disposed within a groove, or those elastic strands that are to be severed may be disposed within one or more grooves. The location of the grooves may be predetermined and, therefore, the location of the elastic strands may be known. Alternatively or in addition to the aforementioned, a high speed camera may be used to detect the position of the elastic strands. The position of the elastic strands may then be communicated to the laser source and the laser source may be operated accordingly.

FIG. 15 illustrates a first laser source 322 and a second laser source 324 adjacent a belt assembly 304 including a body substrate 316. In some embodiments, the first laser source 322 may be used to sever one or more elastic strands 168 to form a gap 330 in the elastic strands. To sever the one or more elastic strands 322, the first laser source may be pulsed, so that the laser source is powered on while it is disposed over an elastic strand and powered off while it is not disposed over an elastic strand. Alternatively, or in addition to pulsing the laser source, a mask may be used to control which portions of the substrate the laser source may affect. The pulsing of the laser source and the use of a mask may also be used in combination with an outer circumferential surface having one or more grooves to aid in locating the elastic strands that should be severed. A second laser source 324 may be used to impart a line of weakness. As illustrated in FIG. 15, the second laser source 324 may impart a discrete line of weakness 224 into the body substrate 316. It is also to be appreciated that one or more continuous lines of weakness may also, or alternatively, be imparted into the body substrate 316 by the second laser source 324. The second laser source 324 may traverse in the cross direction CD to a second position. In the second position, the second laser source 324 may also be used to sever one or more elastic strands to form a gap 330 in the elastic strands. The one or more elastic strands 168 may be severed in any manner as previously discussed.

It is to be appreciated that when severing the elastic strands, it is desirable to minimize the destruction by controlling the exposure of the substrate layers to the laser source and to ensure that the elastic strands are separated. Stated another way, the intent is to sever the elastic strand prior to separating all nonwoven fibers. Generally, the nonwoven substrate that is disposed between the laser source and the elastic strand will degrade, such as by melting and/or ablating, prior to the elastic strand due to the properties of the nonwoven substrate and the elastic strand. More specifically, each different material has a wavelength or range of wavelengths at which its absorptivity is greatest or optimal. Thus, a laser source may be chosen such that the wavelength emitted by the laser beam is more readily absorbed by the elastic strands than the nonwoven substrate. In this case, the elastic strands may break prior to all the fibers of the nonwoven substrate separating. It is to be appreciated that the elastic strands may be under tension when they are acted on by the laser source. Elastics under tension want to relax. This property of the elastic strands may also aid in cutting the elastic strand prior to the breaking all the fibers of the nonwoven substrate.

However, materials may be altered to increase their absorptivity even if the laser source is operating outside their optimal range of wavelengths. In some embodiments, the elastic strands may be chemically altered such that the elastic strands have an increased rate of energy absorption, or absorptivity. These chemical additives may be added to the material that forms each elastic strand prior to the elastic strand being formed, such as by extrusion or other known methods. These chemicals additives may also be added to the elastic strand after formation. For example, these chemicals may be applied topically to each elastic strand. These chemical additives may also be added to the adhesive that attaches the elastic strand to the nonwoven substrate. Such chemical additives are available from Clearweld, Binghamton, N.Y. These chemical additives may be added to ensure that the elastic strands 168 present in a line of weakness get severed or can be severed by a relatively low force upon separation of the trim from the belt assembly 304, and to ensure that the elastic strands 168 present in the region of the belt assembly 304 are severed while not destroying the substrate layers.

It is also to be appreciated that any number of laser sources may be used to either sever the elastic strands and/or to impart a continuous or discontinuous line of weakness into the belt assembly. For example, a single laser source may be used to impart a continuous or discontinuous line of weakness into the first and second belts 106, 108 and another laser source may be used to sever the elastic strands in both the first and second belts 106, 108.

The laser source 312, as illustrated in FIG. 11, may be any apparatus that produces and amplifies light. More specifically, a laser source may be any apparatus that transforms energy into other forms of electromagnetic radiation, for example light. In some embodiments, the laser source may be a $CO_2$ laser or a Nd:YAG laser. However, any type of laser that is capable of weakening a substrate may be used. The laser source 312 may emit many hundreds of watts which can be concentrated over a relatively small area, also referred to as a focal area. For example, the focal area may be from about 30 μm to about 300 μm, and/or from about 50 μm to about 200 μm, and/or from about 100 μm to about 150 μm, including all 0.1 μm therebetween. However, if a laser source emits too much power, the one or more substrate layers may be cut or severed. The minimum power required to cut a material is referred to as a cutting power. By operating the laser source at less than its cutting power, a line of weakness may be imparted to the one or more substrates. More specifically, to impart a line of weakness, a laser source may be operated from about 98% to about 5% of its cutting power.

For example, a laser source 312 having a total power capacity of 600 watts may act on a belt assembly 304 including a first belt 106 including a first substrate, a second substrate, and elastic strands therebetween, as shown in FIG. 12A. If the laser source 312 having total power capacity of 600 watts is operated at a power of 100%-60% of its total power capacity, the laser source 312 cuts or severs the first belt 106. More specifically, if the total power capacity of the laser source 312 was 600 watts, the laser source 312 would emit 360 watts if it were operating at 60%. A laser source 312 emitting 360 watts cuts or severs the first belt 106. However, below 360 watts, the laser source 312 fails to cut through the first belt. Thus, the laser source has a cutting power of 360 watts. To impart a line of weakness, such as previously disclosed, the laser source 312 operates below 60% of the total power capacity or below 360 watts to impart a line of weakness rather than to cut or sever the belt. The laser source 312 may operate from about 58% to about 24% of its total power capacity, or, stated another way, the laser source may operate below about 98% of its cutting power. In this example, the laser source 312 may emit from about 330 watts to about 150 watts to impart a line of weakness into the belt 106.

Generally, the lower the power emitted by the laser source 312 the fewer the number of separated fibers. The optimal operating settings of the laser source 312 may be such that the laser source does not separate all the fibers present in the nonwoven substrates of the belt assembly 304. The precise settings of the laser source 312 may be dependent, in part, upon the materials into which the laser source is to impart the line of weakness, the type of laser source, and the distance of the laser source from the material or substrate. The aforementioned applies to any laser source discussed herein.

After the laser source 312 acts on the belt assembly 304, the belt assembly 304 may continue to be advanced by the process member 302. Referring to FIG. 11, the belt assembly 304 may be transferred to a second guide roller 314 and advanced toward subsequent processes. The process member 302 may include a pressure source (not shown) that transfers a gas and/or fluid through the one or more apertures 318 causing the belt assembly 304 to be forced away from the outer circumferential surface 308 of the process member 302.

Figure 16:
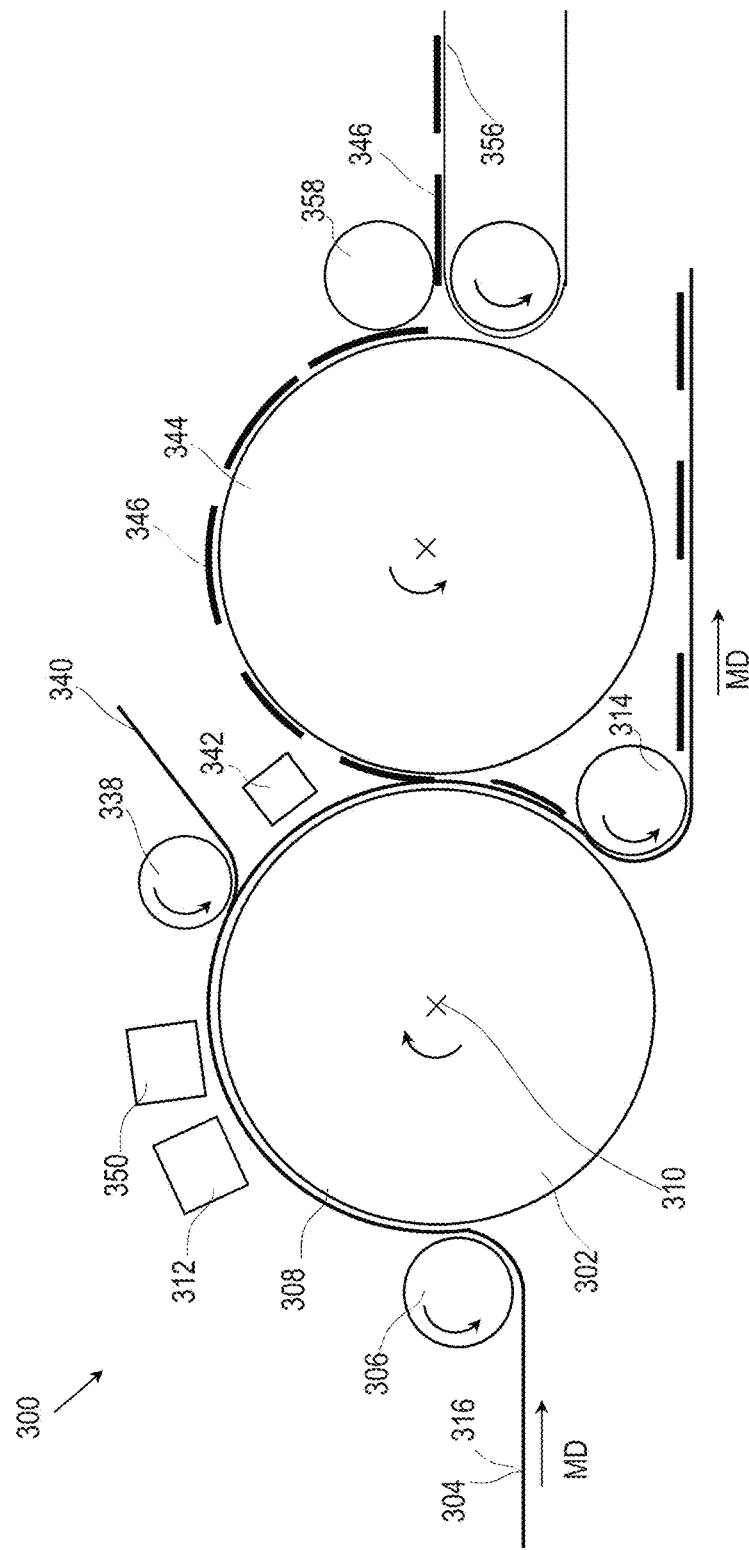
FIG. 16 is a schematic representation of an apparatus that imparts a line of weakness into a substrate in accordance with one non-limiting embodiment of the present disclosure.

As previously discussed, the belt assembly 304 may undergo one or more processes. FIG. 16 illustrates an example embodiment of an apparatus 300 that may be used to manufacture an absorbent article 100. The process member 302 may rotate about a longitudinal axis of rotation 310 and be configured to receive a belt assembly 304, as previously discussed.

The belt assembly 304 may advance in a machine direction MD toward the process member 302. A first guide roller 306 may aid in the transfer of the belt assembly 304 onto an outer circumferential surface 308 of the process member 302. The outer circumferential surface 308 of the process member 302 may include one or more apertures. A vacuum source, not shown, may be in fluid communication with the one or more apertures. The vacuum source allows a gas to be circulated through the one or more apertures toward the longitudinal axis of rotation 310. The movement of fluid may result in the belt assembly 304 being forced toward the outer circumferential surface 308 of the process member 302. The process member 302 may rotate about the longitudinal axis of rotation 310 causing the belt assembly 304 to advance toward a laser source 312, which may include one or more laser sources, as previously discussed. The laser source 312 may be used to impart a discrete line of weakness into the belt assembly 304 or to impart a continuous line of weakness into the belt assembly 304.

The process member 304 may then advance the belt assembly 304 to a cutting member 350. The cutting member 350 may be used to sever one or more elastic strands 168. The cutting member 350 may be an apparatus such as disclosed in U.S. Pat. No. 8,440,043.

Figure 17A:
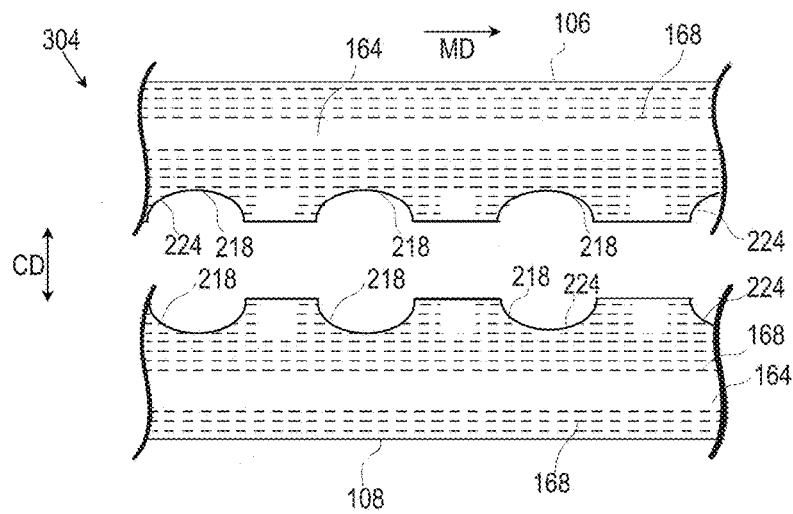
FIG. 17A is a top view of a belt assembly including a discrete separation edge in accordance with one non-limiting embodiment of the present disclosure.
Figure 17B:
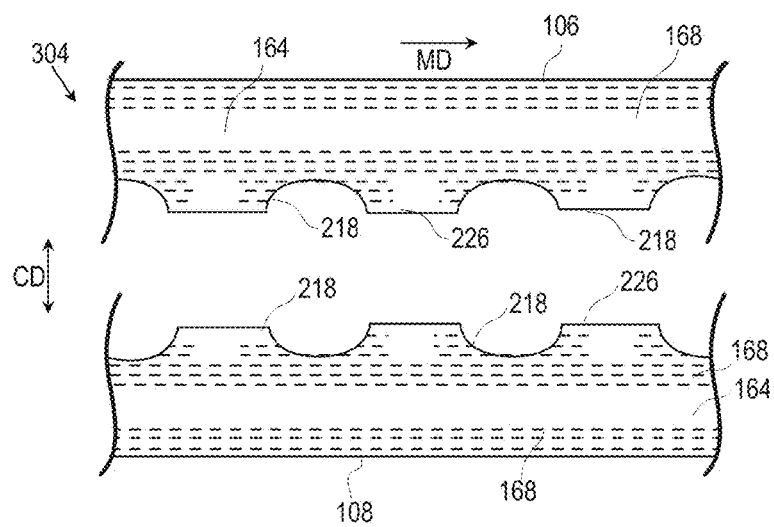
FIG. 17B is a top view of a belt assembly including a continuous separation edge in accordance with one non-limiting embodiment of the present disclosure.

The belt assembly 304 including at least one of a continuous line of weakness and a discrete line of weakness may advance to a trim removal member 338. The trim removal member 338 may remove the trim 340, which may include a discrete portion and/or a continuous portion of the line of weakness, as illustrated in FIGS. 14B and 14C. A trim removal member 338 may apply a force to the discrete or continuous line of weakness to remove continuous lengths of trim as well as discrete pieces of trim that have been weakened by the laser source 312. More particularly, as the first belt 106 and the second belt 108 advances in the machine direction, the trim removal member 338 may be used to separate and remove trim from and/or along either or both opposing side edges of the first belt 106 and the second belt 108. The trim removal member 338 may include an apparatus such as disclosed in U.S. Publ. No. 2012/0079926. Other devices that may be suitable as a trim removal member 338 include a vacuum head including one or more vacuum nozzles, which may be used to separate the trim from the belt assembly, and a duct system, which may be used to transport the trim from the process member to a disposal location. FIGS. 17A-17B illustrate the belt assembly 304 upon removal of the trim 340. Upon removal of the trim 340 a separation edge 218 is formed, such as previously discussed with reference to FIGS. 8, 9A-9B, and 10A-10B.

The belt assembly 304 may then be advanced to an adhesive applicator 342. The adhesive applicator may apply adhesive, such as glue, to the belt assembly 304. The adhesive may be applied to a portion of the first belt 106 and a portion of the second belt 108. The adhesive may be applied to portions of the first belt 106 and the second belt 108 where additional components for the absorbent article are to be added. In some embodiments, the adhesive may be applied to the portion of the belt assembly 304 having severed elastic strands 168.

Upon applying adhesive to at least one of the belt assembly 304, the belt assembly 304 may be advanced to operatively engage with a transfer apparatus 344. The transfer apparatus 344 may be used to transfer and/or rotate a discrete component 346 of the absorbent article. An example of a discrete component 346 is a chassis 102, such as discussed with reference to FIGS. 2 and 4. In some embodiments, the transfer apparatus 344 may receive a discrete component 346 positioned in a first orientation 352, as illustrated in FIG. 18A. More specifically, the discrete component 346 may be orientated in a first orientation 352 when the longitudinal axis 124 of the discrete component 346 is substantially parallel to the machine direction MD and/or substantially perpendicular to the cross direction CD. However, to be disposed on the belt assembly 304, the discrete component 346 may need to be rotated. In the embodiments wherein the discrete component 346 is a chassis 102, the chassis 102 may need to be rotated so that a first portion of the chassis 102 is disposed on the first belt 106 and a second portion of the chassis 102 is disposed on the second belt 108. Thus, the transfer apparatus 344 may be configured to transfer the discrete component 346 from a first carrier member 356, which may include a conveyor belt supported by one or more guide rollers. More specifically, a third guide roller 358 may be used to aid in transferring the discrete component 346 onto the outer circumferential surface 360 of the transfer member 344. The transfer member 344 may advance the discrete component 346 to a position that allows the discrete component 346 to be disposed on the belt assembly 304. In some embodiments, the transfer member 344 may also rotate the discrete component to a second orientation 354, as illustrated in FIG. 18B. More specifically, the discrete component 346 may be orientated in a second orientation 352 when the longitudinal axis 124 of the discrete component 346 is substantially perpendicular to the machine direction MD and/or substantially parallel to the cross direction CD. It is to be appreciated that the discrete component 346 may not be rotated or may be rotated in any position that allows the discrete component 346 to be orientated in a desired position. The transfer member 344 may be an apparatus such as that disclosed in U.S. Pat. No. 8,820,513.

As illustrated in FIG. 16, the transfer member 344 may be operatively engaged with the process member 302. More specifically, as the belt assembly 304 rotates about the longitudinal axis of rotation 310, the transfer member 344 may transfer a discrete component 346 onto at least a portion of the belt assembly 304. In some embodiments, as illustrated in FIG. 18C, the transfer member 344 may transfer a chassis 102 onto a portion of the first belt 106 and a portion of the second belt 108. Stated another way, a first portion of the chassis 102 may be disposed on a portion of the first belt 106 and a second portion of the chassis 102 may be disposed on the portion of the second belt 108. As was previously discussed, an adhesive may be applied to the belt assembly 304. The adhesive may allow the chassis 102 to be adhered to the belt assembly 304, and, thus, be transferred from the transfer member 344 to the process member 302.

Still referring to FIG. 16, the belt assembly 304 including the discrete component 346, such as a chassis 346, may be advanced by the process member 302 to a second guide roller 314. The second guide roll 314 may be used to transfer the belt assembly 304 including the discrete component 346 to additional downstream processes. In some embodiments, the second guide roller 314 may also act as a bonding roll. The second guide roller 314 may be positioned such that pressure is applied to the belt assembly 304 and the discrete component 346 as the combination passes between the second guide roller 314 and the process member 302. The second guide roller 314 may be used to bond the discrete component 346 to the belt assembly 304.

Figure 19:
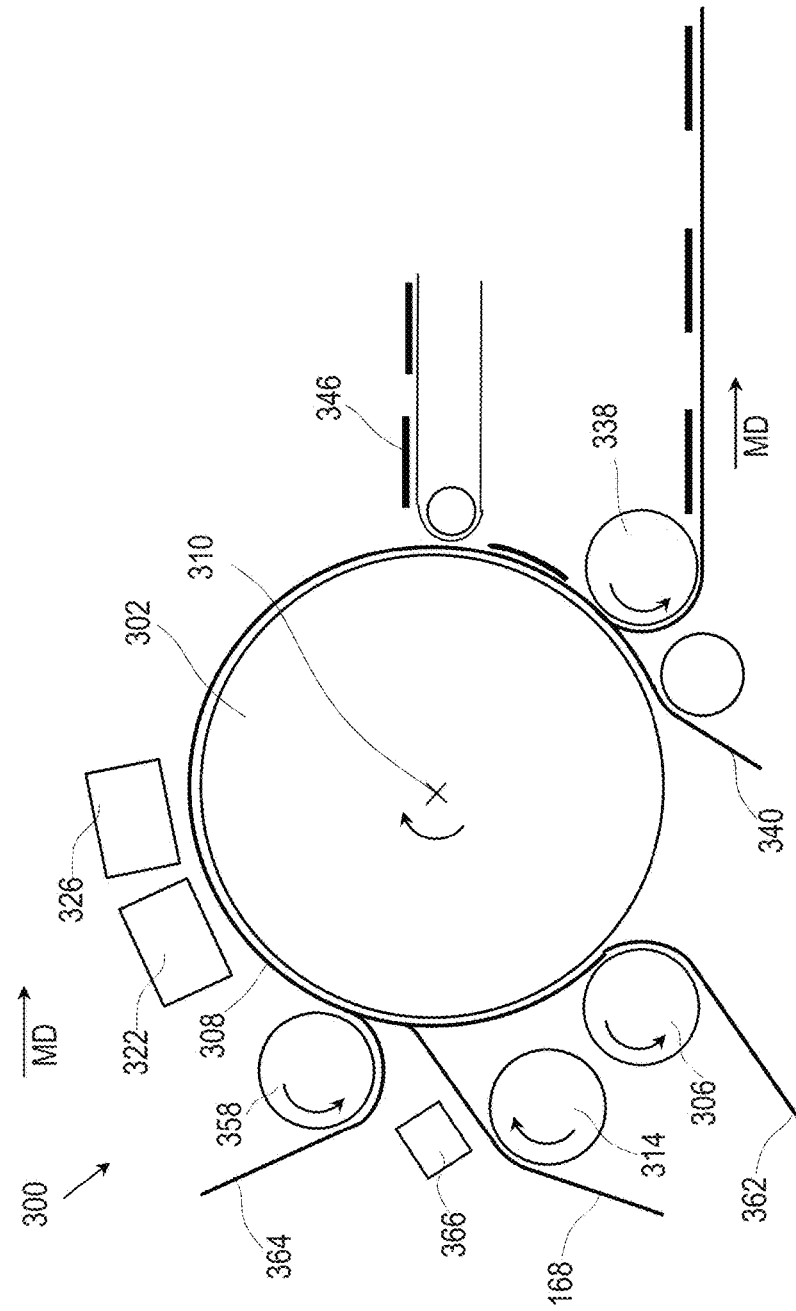
FIG. 19 is a schematic representation of an apparatus that imparts a line of weakness into a substrate in accordance with one non-limiting embodiment of the present disclosure.

As previously discussed, the belt assembly 304 may include a garment facing layer, also referred to as an outer layer, of nonwoven 162 and a wearer facing layer, also referred to as an inner layer, of nonwoven 164 and one or more elastic strands 168 disposed between the outer layer 162 and the inner layer 164. In some embodiments, the belt assembly 304 may be assembled on the outer circumferential surface 308 of the process member 302, as illustrated in FIG. 19. A first continuous substrate layer may correspond with the outer layer 162. A second continuous substrate layer 164 may correspond to an inner layer 164.

As illustrated in FIG. 19, a first continuous substrate layer 362 may be advanced toward the process member 304. The first continuous substrate layer 362 may surround a portion of a first guide roller 306. The first guide roller may aid in advancing and transferring the first continuous substrate layer 362. The first continuous substrate layer 362 may be disposed on the outer circumferential surface 308 of the process member 302. As previously discussed, one or more apertures may be in fluid communication with a vacuum source, which may cause the first continuous substrate 362 to be forced against the outer circumferential surface 308.

Still referring to FIG. 19, one or more elastic strands 168 may be advanced toward the process member 302. The one or more elastic strands 168 may be stretched in the machine direction MD prior to being disposed on the first continuous substrate 362. Further, the one or more elastic strands may be adhered to the first continuous substrate 362. Thus, a second guide roller 314 may be used to advance the one or more elastic strands 168 to an adhesive applicator 366. The adhesive applicator 366 may apply adhesive to the one or more strands 168. The adhesive may be applied continuously over the one or more elastic strands or the adhesive may be applied in discrete sections, or intermittently, over the elastic strands. It is also to be appreciated that the discrete sections of adhesive may extend over the same length or discrete sections may have different lengths. For example, a first discrete section of adhesive may be longer than or shorter than a second discrete section of adhesive. It is also to be appreciated that there may be sections without adhesive, these sections are non-bonded sections. There may be a non-bonded area where the elastic strands are to be severed. The elastic strands including portions having adhesive applied thereto may be disposed on and bonded to the first continuous substrate 362.

It is also to be appreciated that the elastic strands may be disposed on the first continuous substrate 362 prior to adhesive being disposed on the elastic strands. Stated another way, the elastic strands 168 may be disposed on the first continuous substrate 362. The first continuous substrate 362 including the elastic strands 168 may be advance to an adhesive applicator 366. The adhesive applicator 366 may apply the adhesive to the one or more strands 168, which are disposed on the first continuous substrate 362. The elastic strands 168 are bonded to the first continuous substrate 362.

Still referring to FIG. 19, a second continuous substrate 364 may be advanced toward the process member 302. A third guide roller 358 may aid in advancing and transferring the second continuous substrate 364 onto the process member 302. The second continuous substrate 364 may be disposed on the elastic strands 168 and the first continuous substrate 362.

It is to be appreciated that the aforementioned may apply to the formation of both the first belt 106, the second belt 108, and the body substrate 316. With respect to the belt assembly 304, the first belt 106 and the second belt 108 may be assembled adjacent one another in the cross direction CD on the outer circumferential surface 308 of the process member 302.

It is also to be appreciated that assembling the first belt 106, the second belt 108, and/or the body substrate 316 on the outer circumferential surface 308 of the process member 302 may aid in locating the one or more elastic strands 168 for severing. Assembling the belt or substrate on the process member 302 may lead to better control of how and where each component is disposed on the outer circumferential surface. Further, a portion of the adhesive may transfer through the first continuous layer causing some adhesion to the outer circumferential surface 308, which may cause the elastic strands to remain in relatively the same location for subsequent processing. Once the belt assembly 304 has been assembled, the belt assembly 304 may proceed to additional processes, as previously discussed.

FIG. 19 also illustrates embodiments wherein a discrete component 346 may be disposed on the belt assembly 304 prior to the trim 340 being removed from the belt assembly 304. More specifically, a laser source 322, 326 may impart a line or weakness into the belt assembly 304. Further, one or more discrete components 346 may be disposed on the belt assembly 304. Subsequently, the belt assembly 304 may be advanced such that a trim removal member 338 engages the belt assembly 304 causing the discrete and/or continuous trim 340 to remain engaged with the outer circumferential surface 308 of the process member 302 and for the remainder of the belt assembly 304 including the discrete component 346 to diverge from the outer circumferential surface 308 of the process member 304 and advance in a machine direction MD away from the process member 304. As previously discussed, the trim removal member 338 may be an apparatus such as disclosed in U.S. Publ. No. 2012/0079926.

Although much of the present disclosure is provided in the context of manufacturing absorbent articles, it is to be appreciated that the apparatuses and methods disclosed herein may be applied to the manufacture of other types of articles and products manufactured from continuous substrates. Examples of other products include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets, pre-moistened wipes or pads, pre-moistened cloths, paper towels, dryer sheets and dry-cleaning clothes such. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers, training and pull-on pants, adult incontinence briefs and undergarments, feminine hygiene garments such as panty liners, absorbent inserts, and the like, toilet paper, tissue paper, facial wipes or clothes, and toilet training wipes. Still other examples of products may include packaging components and substrates and/or containers for laundry detergent, which may be produced in pellets or pouches and may be manufactured in a converting or web process or even discreet products produced at high speed such as high-speed bottling lines, cosmetics, razor blade cartridges, and disposable consumer batteries.

It is also to be appreciated that the separation edge 218 and/or the cut edge 202 may be softened mechanically after being acted on by the laser source. The accumulated material or clusters of accumulated material lead to the edge feeling rough or sharp. Generally, the skin perceives a nonwoven edge as soft if the end of fibers produces a small amplitude wave and little periodicity. The skin perceives an edge as rough if the amplitude and periodicity of the wave produced between the skin and fiber ends is other than flat. The higher the amplitude and the shorter the period, the rougher the edge feels.

The laser source ablated a portion of the individual fiber ends and melted the individual fiber ends that were in proximity to the ablated portion. Thus, the individual fibers that underwent melting include an accumulation of material at the tip, also referred to as a sphere of material. This sphere of material may be three to four times the diameter of the individual fiber that did not undergo melting or was not ablated.

The size of the individual fibers that have undergone melting may be increased as they are joined together. For example, a medium size cluster may be formed by more than two fiber-ends melted together. This medium size cluster forms a larger sphere having a diameter greater than three times or greater than about four times the diameter of an individual fiber diameter. Clusters of material form a linear, seemingly high density edge, at least as thick as the nonwoven composite caliper. Thus, it is important that these clusters may be broken up before use in an absorbent article.

In some embodiments, the separation edge or the cut edge may be fed through two rollers. The two rollers exert pressure on the edge causing the edge to be strained. The straining of the edge breaks up some of these clusters of accumulated material resulting in a relatively softer feeling edge. The material of the surface of the rollers may be important to induce the required strain on the edge to remove the clusters. It is also to be appreciated that the material may be chosen such that the elastic strands that are fed between the nip of the two rollers do not get damaged in the process of straining the edge. For example, a first roller may have a metal surface and a second roller may have a rubber surface. Further, the first roller may have a substantially smooth surface or the first roller may have a pattern.

In some embodiments, the edge may be activated, such as by ring rolling as disclosed in U.S. Pat. No. 4,116,892, or by plate activation as disclosed in U.S. Pat. No. 6,500,377. Activating the edge may also reduce the rough or sharp feeling of the edge due to breaking up the clusters of accumulated material. The amount of cluster break up during this process may be due in part to the tooth tip radius, the distance between adjacent teeth, the tooth height, the tooth wall angle, the temperature, and depth of tooth engagement.

Figure 20:
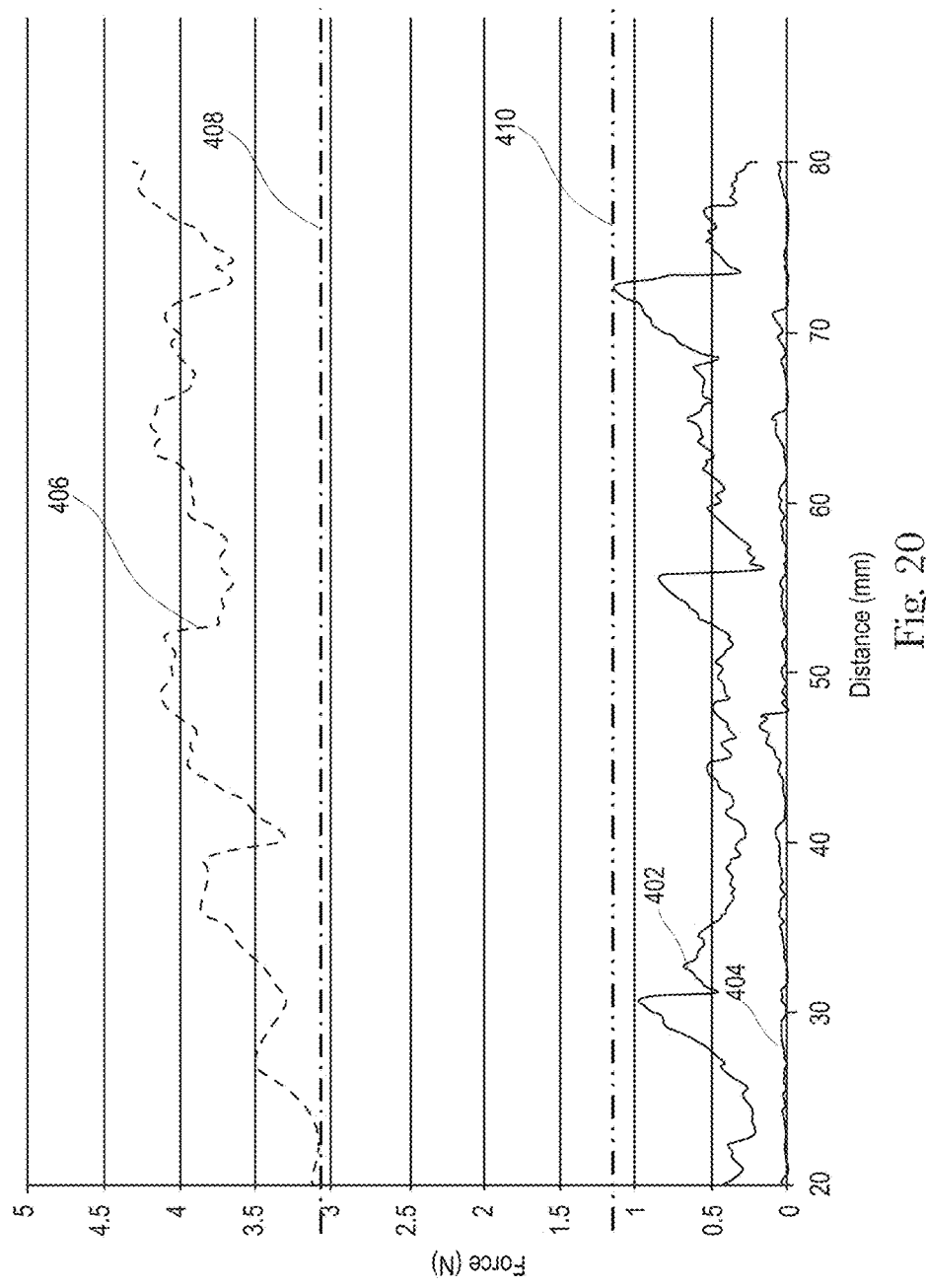
FIG. 20 is a graphical illustration of the force required to separate a laminate in accordance with one non-limiting embodiment of the present disclosure.

As previously discussed, the line of weakness imparted to the substrate requires subsequent separation. The force required to separate the substrate along the line of weakness depends, in part, on the characteristics of the line of weakness. Generally, the greater the number of fibers severed by the laser source, the easier the substrate will be to separate along the line of weakness. FIG. 20 illustrates this concept.

FIG. 20 illustrates the separation force required to separate a laminate with and without a line of weakness. More specifically, a $CO_2$ type laser source having a total power capacity of 600 watts was used to impart a line of weakness into a laminate. The laminate included two substrate layers. Each of the substrate layers were made from spunbond polypropylene to from a nonwoven and each layer had a basis weight of about 20 gsm. The two substrate layers were held together with a construction adhesive, such as Dispomelt 526, having a basis weight of 6 gsm. The laminate was passed through the laser source at a speed of about 500 m/min and the focal area of the laser beam being emitted by the laser source was 140 μm. The laser source was used to impart a first line of weakness into a first laminate. To impart the first line of weakness, the laser source emitted a power output of about 180 watts. The laser source was then used to impart a second line of weakness into a second laminate. To impart the second line of weakness, the laser source emitted a power output of 270 watts. A first separation force 402 was applied to the first laminate to separate the first line of weakness. The change in the first separation force 402 as the first laminate was separated along the first line of weakness is illustrated in FIG. 20. A second separation force 404 was applied to the second laminate to separate the second line of weakness. The change in the second separation force 404 as the second laminate was separated along the second line of weakness is also illustrated in FIG. 20. For purposes of comparison, a third separation force 406 was applied to a third laminate that was not acted on by the laser source and, thus, did not include a line of weakness. The change in the third separation force 406 as the third laminate was separated is also illustrated in FIG. 20.

As shown in FIG. 20, imparting a line of weakness into the laminate reduces the amount of force required to separate a laminate. Further, by increasing the power of the laser source, the amount of force required to separate the laminate along the line of weakness was reduced. However, it is to be appreciated that by increasing the power of the laser source, the accumulated material and/or clusters along the separation edge may increase. The optimal characteristics of the line of weakness imparted to a substrate may depend, in part, on the force required to separate the substrate along the line of weakness and the characteristics of the separation edge.

The line of weakness imparted to the laminate or other substrate(s) may be such that the force required to separate the laminate or other substrate(s) is less than the force required to separate the laminate or other substrate(s) that have no line of weakness. For example, as illustrated in FIG. 20, a third separation force 406 was required to separate the third laminate, and the third laminate included no line of weakness. The lowest point on the third separation force 406 curve is illustrated within minimum force line 408. It is to be appreciated that the separation force required to separate any line of weakness imparted to a laminate or other substrate(s) be below the minimum force line for that particular laminate or substrate(s). For example, as illustrated in FIG. 20, for the second laminate, the second separation force 404 was plotted as the line of weakness imparted to the second laminate was separated. This second separation force 404 includes a maximum force line 410, which intersects the greatest force required during the separation of the second laminate. As illustrated, the maximum force line 410 is below or less than the minimum force line 408.

If the maximum force line 410 was above or greater than the minimum force line 410, this may be evidence that the substrate(s) or laminate has separated in an area other than the line of weakness. The line of weakness may be used to control where the substrate(s) or laminate separate. Further, this may be evidence that the laser source is improper for the given substrate(s) or laminate. For example, the laser source is not strong enough to impart a proper line of weakness into the substrate(s) or laminate.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacturing an absorbent article, the method comprising:
   advancing a discrete component on a carrier member;
   rotating a transfer member about a first axis of rotation;
   accepting the discrete article on the transfer member;
   advancing a first substrate, a second substrate, and one or more elastic strands toward a process member;
   receiving the second substrate on an outer circumferential surface of the process member, wherein the process member rotates about a longitudinal axis of rotation;
   attaching at least a portion of the one or more elastic strands to the first substrate;
   disposing the second substrate on at least a portion of the one or more elastic strands and the first substrate to form a belt assembly;
   advancing the belt assembly to a first laser source, where the first laser source imparts a line of weakness on the belt assembly;
   advancing the belt assembly including the discrete component to a trim removal apparatus, wherein the trim removal apparatus removes trim from the line of weakness forming a separation edge;
   advancing the belt assembly to a second laser source, wherein the second laser source severs a portion of the one or more elastic strands forming a gap in the elastic strands at an elastic gap location that is spaced apart from the line of weakness; and positioning the discrete component on a portion of the belt assembly.

2. The method of claim 1, wherein the line of weakness includes one or more discrete lines of weakness.

3. The method of claim 1, wherein the line of weakness is a continuous line of weakness.

4. The method of claim 1, wherein the process member includes one or more apertures, wherein the one or more apertures are configured to circulate a gas toward the longitudinal axis of rotation.

5. The method of claim 1, wherein the outer circumferential surface of the process member comprises one or more grooves.

6. The method of claim 5, further comprising the step of positioning one or more of the one or more elastic strands within the one or more grooves.

7. The method of claim 1, wherein the first and second substrates are intact at the elastic gap location.

8. A method for manufacturing an absorbent article, the method comprising:
advancing a belt assembly around a portion of a first guide roller, wherein the belt assembly comprises an outer substrate, an inner substrate, and one or more elastic strands disposed between the outer substrate and the inner substrate;
disposing the outer substrate of the belt assembly on an outer circumferential surface of a process member;
rotating the process member about a longitudinal axis of rotation;
advancing the belt assembly to a first laser source, wherein the first laser source imparts a line of weakness into the belt assembly;
advancing the belt assembly to a trim removal member, wherein the trim removal member separates the line of weakness forming a trim portion and a separation edge;
advancing the belt assembly to a second laser source, wherein the second laser source severs a portion of the one or more elastic strands forming a gap in the elastic strands at an elastic gap location that is spaced apart from the line of weakness;
advancing a discrete component toward the process member;
orienting the discrete component; and
positioning the discrete component on a portion of the belt assembly.

9. The method of claim 8, wherein the discrete component is oriented by a transfer member.

10. The method of claim 8, wherein the belt assembly comprises a first belt and a second belt.

11. The method of claim 8, wherein the belt assembly comprises a body substrate.

12. The method of claim 8, wherein the line of weakness comprises at least one of one or more discrete lines of weakness and a continuous line of weakness.

13. The method of claim 8, wherein the inner and outer substrates are intact at the elastic gap location.

14. A method for manufacturing an absorbent article, the method comprising:
advancing a belt assembly in a machine direction, wherein the belt assembly comprises an outer layer, an inner layer, and one or more elastic strands disposed between the outer layer and the inner layer;
disposing the outer layer of the belt assembly on an outer circumferential surface of a process member;
rotating the process member about a longitudinal axis of rotation;
advancing the belt assembly to a first laser source, wherein the first laser source imparts a line of weakness into the belt assembly;
advancing the belt assembly to a cutting member, wherein the cutting member severs a portion of the one or more elastic strands forming a gap in the elastic strands at an elastic gap location that is spaced apart from the line of weakness; and
advancing the belt assembly to a trim removal member, wherein the trim removal member separates the line of weakness forming a trim portion and a separation edge.

15. The method of claim 14, further comprising: advancing a discrete component toward the process member; orienting the discrete component; and positioning the discrete component on a portion of the belt assembly.

16. The method of claim 14, further comprising the step of advancing the separation edge of the belt assembly through a nip formed by a first roller and a second roller, wherein the first roller and the second roller strain the separation edge of the belt assembly.

17. The method of claim 14, further comprising positioning a mask between the first laser source and the belt assembly.

18. The method of claim 14, wherein the outer circumferential surface of the process member comprises one or more grooves configured to accept one or more elastic strands.

19. The method of claim 14, wherein the laser source is operated below a cutting power.

20. The method of claim 14, further comprising the steps of: applying an adhesive to a portion of the belt assembly; and adding a chemical additive to a portion of the one or more elastic strands.

21. The method of claim 14, further comprising the step of activating the separation edge.

22. The method of claim 14, wherein the inner and outer layers are intact at the elastic gap location.

* * * * *